(12) United States Patent
Gerberding et al.

(10) Patent No.: US 10,285,709 B2
(45) Date of Patent: *May 14, 2019

(54) SYSTEMS AND METHODS FOR SUPPORTING OR OCCLUDING A PHYSIOLOGICAL OPENING OR CAVITY

(71) Applicant: Pulsar Vascular, Inc., San Jose, CA (US)

(72) Inventors: Brent Gerberding, San Jose, CA (US); Robert M. Abrams, Los Gatos, CA (US); Gilbert Clarke, Seattle, WA (US)

(73) Assignee: Pulsar Vascular, Inc., San Jose ( * ) Notice: Subject to any disclaimer, the term of this patent is extended or adjusted under 35 U.S.C. 154(b) by 42 days.

This patent is subject to a terminal disclaimer.

(21) Appl. No.: 15/161,032

(22) Filed: May 20, 2016

(65) Prior Publication Data

US 2016/0262765 A1    Sep. 15, 2016

Related U.S. Application Data

(60) Continuation of application No. 14/618,969, filed on Feb. 10, 2015, now Pat. No. 9,615,831, which is a
(Continued)

(51) Int. Cl.
*A61B 17/12* (2006.01)
*A61F 2/06* (2013.01)
(Continued)

(52) U.S. Cl.
CPC .. *A61B 17/12113* (2013.01); *A61B 17/12022* (2013.01); *A61B 17/12036* (2013.01);
(Continued)

(58) Field of Classification Search
CPC ........ A61B 17/12113; A61B 17/12118; A61B 17/12172; A61B 17/12177; A61F 2/86; A61F 2/95

See application file for complete search history.

(56) References Cited

U.S. PATENT DOCUMENTS 3,868,956 A   3/1975 Alfidi et al.
4,164,045 A   8/1979 Bokros et al.
(Continued)

FOREIGN PATENT DOCUMENTS

CN   1384726   12/2002
CN   1399530    2/2003
(Continued)

OTHER PUBLICATIONS

Cordis NeuroVascular, Inc.; "Masstransit Microcatheter," Product Brochure; No. 153-8383-3; Miami Lakes, FL, USA (2003).
(Continued)

*Primary Examiner* — Alexander J Orkin
(74) *Attorney, Agent, or Firm* — Troutman Sanders LLP

(57) ABSTRACT

Implantable devices for placement at a cavity or opening such as an aneurysm are disclosed. The implantable devices, in a deployed condition, have a generally inverted U-shaped profile with a curved or angled framework support structure sized and configured for placement in proximity to tissue surrounding the opening and anchoring legs extending proximally from the framework structure sized and configured to contact the wall of a neighboring lumen at opposed locations. Occlusive and semi-occlusive membranes may be associated with the framework support structure and deployed over the opening to provide exclusion of the opening and flow diversion. Proximal anchoring segments providing additional lumen wall surface area contact for the implantable device following deployment may be incorporated.

8 Claims, 20 Drawing Sheets

Related U.S. Application Data continuation of application No. 13/774,759, filed on Feb. 22, 2013, now Pat. No. 8,979,893, which is a division of application No. 12/554,850, filed on Sep. 4, 2009, now Pat. No. 8,388,650.

(60) Provisional application No. 61/094,693, filed on Sep. 5, 2008.

(51) Int. Cl.
   *A61F 2/95* (2013.01)
   *A61F 2/86* (2013.01)
   *A61B 17/00* (2006.01)

(52) U.S. Cl.
   CPC .. *A61B 17/12118* (2013.01); *A61B 17/12172* (2013.01); *A61B 17/12177* (2013.01); *A61F 2/06* (2013.01); *A61F 2/86* (2013.01); *A61F 2/95* (2013.01); *A61B 2017/00778* (2013.01); *A61B 2017/00867* (2013.01); *A61B 2017/00893* (2013.01); *A61B 2017/00898* (2013.01); *A61B 2017/12054* (2013.01); *A61F 2240/001* (2013.01)

(56) References Cited

U.S. PATENT DOCUMENTS

| | | |
|---|---|---|
| 4,248,234 A | 2/1981 | Assenza et al. |
| 4,645,495 A | 2/1987 | Vaillancourt |
| 4,651,751 A | 3/1987 | Swendson et al. |
| 4,665,906 A | 5/1987 | Jervis |
| 4,706,671 A | 11/1987 | Weinrib |
| 4,710,192 A | 12/1987 | Liotta et al. |
| 4,739,768 A | 4/1988 | Engelson |
| 4,820,298 A | 4/1989 | Leveen et al. |
| 4,873,978 A | 10/1989 | Ginsburg |
| 4,909,787 A | 3/1990 | Danforth |
| 4,994,069 A | 2/1991 | Ritchart et al. |
| 5,011,488 A | 4/1991 | Ginsburg |
| 5,074,869 A | 12/1991 | Daicoff |
| 5,122,136 A | 6/1992 | Guglielmi |
| 5,226,911 A | 7/1993 | Chee et al. |
| 5,250,071 A | 10/1993 | Palermo |
| 5,261,916 A | 11/1993 | Engelson |
| 5,263,964 A | 11/1993 | Purdy |
| 5,263,974 A | 11/1993 | Matsutani et al. |
| 5,271,414 A | 12/1993 | Partika et al. |
| 5,304,195 A | 4/1994 | Twyford et al. |
| 5,334,168 A | 8/1994 | Hemmer |
| 5,342,386 A | 8/1994 | Trotta |
| 5,350,397 A | 9/1994 | Palermo et al. |
| 5,354,295 A | 10/1994 | Guglielmi et al. |
| 5,527,338 A | 6/1996 | Purdy |
| 5,531,685 A | 7/1996 | Hemmer et al. |
| 5,578,074 A | 11/1996 | Mirigian |
| 5,624,449 A | 4/1997 | Pham et al. |
| 5,643,254 A | 7/1997 | Scheldrup et al. |
| 5,665,106 A | 9/1997 | Hammerslag |
| 5,669,931 A | 9/1997 | Kupiecki et al. |
| 5,693,067 A | 12/1997 | Purdy |
| 5,733,294 A | 3/1998 | Forber et al. |
| 5,733,329 A | 3/1998 | Wallace et al. |
| 5,749,890 A | 5/1998 | Shaknovich |
| 5,749,894 A | 5/1998 | Engelson |
| 5,759,194 A | 6/1998 | Hammerslag |
| 5,766,192 A | 6/1998 | Zacca |
| 5,769,884 A | 6/1998 | Solovay |
| 5,797,953 A | 8/1998 | Tekulve |
| 5,814,062 A | 9/1998 | Sepetka et al. |
| 5,843,103 A | 12/1998 | Wulfman |
| D407,818 S | 4/1999 | Mariant et al. |
| 5,895,391 A | 4/1999 | Farnholtz |
| 5,895,410 A | 4/1999 | Forber et al. |
| 5,910,145 A | 6/1999 | Fischell et al. |
| 5,911,737 A | 6/1999 | Lee et al. |
| 5,916,235 A | 6/1999 | Guglielmi |
| 5,925,060 A | 7/1999 | Forber |
| 5,925,062 A | 7/1999 | Purdy |
| 5,925,683 A | 7/1999 | Park |
| 5,928,260 A | 7/1999 | Chin et al. |
| 5,933,329 A | 8/1999 | Tijanoc et al. |
| 5,935,114 A | 8/1999 | Jang et al. |
| 5,935,148 A | 8/1999 | Villar et al. |
| 5,951,599 A | 9/1999 | McCrory |
| 5,968,068 A | 10/1999 | Dehdashtian et al. |
| 5,980,514 A | 11/1999 | Kupiecki et al. |
| 5,980,554 A | 11/1999 | Lenker et al. |
| 5,984,944 A | 11/1999 | Farber |
| 6,007,544 A | 12/1999 | Kim |
| 6,013,055 A | 1/2000 | Bampos et al. |
| 6,022,341 A | 2/2000 | Lentz |
| 6,036,720 A | 3/2000 | Abrams et al. |
| 6,063,070 A | 5/2000 | Eder |
| 6,063,104 A | 5/2000 | Villar et al. |
| 6,071,263 A | 6/2000 | Kirkman |
| 6,077,291 A | 6/2000 | Das |
| 6,081,263 A | 6/2000 | LeGall et al. |
| 6,090,125 A | 7/2000 | Horton |
| 6,093,199 A | 7/2000 | Brown et al. |
| 6,096,021 A | 8/2000 | Helm et al. |
| 6,096,034 A | 8/2000 | Kupiecki et al. |
| 6,102,917 A | 8/2000 | Maitland et al. |
| 6,110,191 A | 8/2000 | Dehdashtian et al. |
| 6,117,157 A | 9/2000 | Tekulve |
| 6,139,564 A | 10/2000 | Teoh |
| 6,146,339 A | 11/2000 | Biagtan et al. |
| 6,152,944 A | 11/2000 | Holman et al. |
| 6,168,615 B1 | 1/2001 | Ken et al. |
| 6,168,622 B1 | 1/2001 | Mazzocchi |
| 6,174,322 B1 | 1/2001 | Schneidt |
| 6,183,495 B1 | 2/2001 | Lenker et al. |
| 6,193,708 B1 | 2/2001 | Ken et al. |
| RE37,117 E | 3/2001 | Palermo |
| 6,221,066 B1 | 4/2001 | Ferrera et al. |
| 6,221,086 B1 | 4/2001 | Forber |
| 6,224,610 B1 | 5/2001 | Ferrera |
| 6,228,052 B1 | 5/2001 | Pohndorf |
| 6,261,305 B1 | 7/2001 | Marotta et al. |
| 6,293,960 B1 | 9/2001 | Ken |
| 6,296,622 B1 | 10/2001 | Kurz et al. |
| 6,309,367 B1 | 10/2001 | Boock |
| 6,325,807 B1 | 12/2001 | Que |
| 6,344,041 B1 | 2/2002 | Kupiecki et al. |
| 6,344,048 B1 | 2/2002 | Chin et al. |
| 6,361,558 B1 | 3/2002 | Hieshima et al. |
| 6,375,668 B1 | 4/2002 | Gifford et al. |
| 6,383,174 B1 | 5/2002 | Eder |
| 6,398,791 B1 | 6/2002 | Que et al. |
| 6,478,773 B1 | 11/2002 | Gandhi et al. |
| 6,491,711 B1 | 12/2002 | Durcan |
| 6,517,515 B1 | 2/2003 | Eidenschink |
| 6,530,935 B2 | 3/2003 | Wensel et al. |
| 6,533,905 B2 | 3/2003 | Johnson et al. |
| 6,554,794 B1 | 4/2003 | Mueller |
| 6,589,256 B2 | 7/2003 | Forber |
| 6,592,605 B2 | 7/2003 | Lenker et al. |
| 6,613,074 B1 | 9/2003 | Mitelberg et al. |
| 6,616,681 B2 | 9/2003 | Hanson et al. |
| 6,626,889 B1 | 9/2003 | Simpson et al. |
| 6,626,928 B1 | 9/2003 | Raymond |
| 6,638,268 B2 | 10/2003 | Niazi |
| 6,652,556 B1 | 11/2003 | VanTassel et al. |
| 6,663,607 B2 | 12/2003 | Slaikeu et al. |
| 6,663,648 B1 | 12/2003 | Trotta |
| 6,669,795 B2 | 12/2003 | Johnson et al. |
| 6,672,338 B1 | 1/2004 | Esashi et al. |
| 6,679,836 B2 | 1/2004 | Couvillon |
| 6,679,903 B2 | 1/2004 | Kurz |
| 6,689,141 B2 | 2/2004 | Ferrera et al. |
| 6,694,979 B2 | 2/2004 | Deem et al. |
| 6,723,112 B2 | 4/2004 | Ho et al. |
| 6,740,073 B1 | 5/2004 | Saville |
| 6,740,277 B2 | 5/2004 | Howell et al. |

(56) References Cited

U.S. PATENT DOCUMENTS

| | | |
|---|---|---|
| 6,746,468 B1 | 6/2004 | Sepetka et al. |
| 6,780,196 B2 | 8/2004 | Chin et al. |
| 6,790,218 B2 | 9/2004 | Jayaraman |
| 6,802,851 B2 | 10/2004 | Jones et al. |
| 6,811,560 B2 | 11/2004 | Jones et al. |
| 6,824,553 B1 | 11/2004 | Samson et al. |
| 6,835,185 B2 | 12/2004 | Ramzipoor et al. |
| 6,837,870 B2 | 1/2005 | Duchamp |
| 6,843,802 B1 | 1/2005 | Villalobos et al. |
| 6,855,153 B2 | 2/2005 | Saadat |
| 6,863,678 B2 | 3/2005 | Lee et al. |
| 6,890,218 B2 | 5/2005 | Patwardhan et al. |
| 6,911,037 B2 | 6/2005 | Gainor et al. |
| 6,936,055 B1 | 8/2005 | Ken et al. |
| 6,939,055 B2 | 9/2005 | Durrant et al. |
| 6,986,774 B2 | 1/2006 | Middleman et al. |
| 6,994,092 B2 | 2/2006 | van der Burg et al. |
| 7,011,094 B2 | 3/2006 | Rapacki et al. |
| 7,033,374 B2 | 4/2006 | Schaefer et al. |
| 7,033,387 B2 | 4/2006 | Zadno-Azizi et al. |
| 7,122,043 B2 | 10/2006 | Greenhalgh et al. |
| 7,147,659 B2 | 12/2006 | Jones |
| 7,156,871 B2 | 1/2007 | Jones et al. |
| 7,169,177 B2 | 1/2007 | Obara |
| 7,229,461 B2 | 6/2007 | Chin et al. |
| 7,232,461 B2 | 6/2007 | Ramer |
| 7,267,679 B2 | 9/2007 | McGuckin et al. |
| 7,306,622 B2 | 12/2007 | Jones et al. |
| 7,322,960 B2 | 1/2008 | Yamamoto et al. |
| 7,343,856 B2 | 3/2008 | Blöhdorn |
| 7,387,629 B2 | 6/2008 | Vanney et al. |
| 7,410,482 B2 | 8/2008 | Murphy et al. |
| 7,569,066 B2 | 8/2009 | Gerberding et al. |
| 7,608,088 B2 | 10/2009 | Jones et al. |
| 7,662,168 B2 | 2/2010 | McGuckin et al. |
| 7,857,825 B2 | 12/2010 | Moran et al. |
| 7,892,254 B2 | 2/2011 | Klint et al. |
| 8,016,853 B2 | 9/2011 | Griffen et al. |
| 8,075,585 B2 | 12/2011 | Lee et al. |
| 8,187,315 B1 | 5/2012 | Clauson et al. |
| 8,262,692 B2 | 9/2012 | Rudakov |
| 8,388,650 B2 | 3/2013 | Gerberding et al. |
| 8,444,667 B2 | 5/2013 | Porter |
| 8,470,013 B2 | 6/2013 | Duggal et al. |
| 8,540,763 B2 | 9/2013 | Jones et al. |
| 8,545,530 B2 | 10/2013 | Eskridge et al. |
| 8,551,132 B2 | 10/2013 | Eskridge et al. |
| 8,556,953 B2 | 10/2013 | Berez et al. |
| 8,715,312 B2 | 5/2014 | Burke et al. |
| 8,715,338 B2 | 5/2014 | Frid |
| 8,728,141 B2 | 5/2014 | Riina et al. |
| 8,747,430 B2 | 6/2014 | Porter |
| 8,771,341 B2 | 7/2014 | Strauss et al. |
| 8,915,950 B2 | 12/2014 | Cam et al. |
| 8,926,680 B2 | 1/2015 | Ferrera et al. |
| 8,956,399 B2 | 2/2015 | Cam et al. |
| 8,979,893 B2 | 3/2015 | Gerberding et al. |
| 9,060,886 B2 | 6/2015 | Molaei et al. |
| 9,107,670 B2 | 8/2015 | Hannes et al. |
| 9,119,625 B2 | 9/2015 | Bachman et al. |
| 9,179,918 B2 | 11/2015 | Levy et al. |
| 9,186,267 B2 | 11/2015 | Losordo et al. |
| 9,192,388 B2 | 11/2015 | Cam et al. |
| 9,211,124 B2 | 12/2015 | Campbell et al. |
| 9,259,229 B2 | 2/2016 | Abrams et al. |
| 9,277,924 B2 | 3/2016 | Clarke et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,831 B2 | 4/2017 | Gerberding et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Peterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 2002/0026232 A1 | 2/2002 | Marotta et al. |
| 2003/0033003 A1 | 2/2003 | Harrison et al. |
| 2003/0057156 A1 | 3/2003 | Peterson et al. |
| 2003/0139802 A1 | 7/2003 | Wulfman et al. |
| 2003/0171730 A1 | 9/2003 | Kelly et al. |
| 2003/0181922 A1 | 9/2003 | Alferness |
| 2003/0181942 A1 | 9/2003 | Sutton et al. |
| 2003/0195385 A1 | 10/2003 | DeVore |
| 2003/0195553 A1 | 10/2003 | Wallace et al. |
| 2003/0212412 A1 | 11/2003 | Dillard et al. |
| 2004/0044391 A1 | 3/2004 | Porter |
| 2004/0068314 A1 | 4/2004 | Jones et al. |
| 2004/0087998 A1 | 5/2004 | Lee et al. |
| 2004/0111112 A1 | 6/2004 | Hoffmann |
| 2004/0158311 A1 | 8/2004 | Berhow et al. |
| 2004/0167597 A1 | 8/2004 | Costantino et al. |
| 2004/0167602 A1 | 8/2004 | Fischell et al. |
| 2004/0172056 A1 | 9/2004 | Guterman et al. |
| 2004/0193206 A1 | 9/2004 | Gerberding et al. |
| 2004/0193246 A1 | 9/2004 | Ferrera |
| 2004/0210248 A1 | 10/2004 | Gordon et al. |
| 2004/0210298 A1 | 10/2004 | Rabkin et al. |
| 2005/0021023 A1 | 1/2005 | Guglielmi et al. |
| 2005/0025797 A1 | 2/2005 | Wang et al. |
| 2005/0033349 A1 | 2/2005 | Jones et al. |
| 2005/0033409 A1 | 2/2005 | Burke et al. |
| 2005/0096728 A1 | 5/2005 | Ramer |
| 2005/0177224 A1 | 8/2005 | Fogarty |
| 2006/0004436 A1 | 1/2006 | Amarant et al. |
| 2006/0030929 A1 | 2/2006 | Musbach |
| 2006/0052862 A1 | 3/2006 | Kanamaru et al. |
| 2006/0058837 A1 | 3/2006 | Bose et al. |
| 2006/0064151 A1 | 3/2006 | Guterman et al. |
| 2006/0106418 A1 | 5/2006 | Seibold et al. |

(56) References Cited

U.S. PATENT DOCUMENTS

| | | |
|---|---|---|
| 2006/0200234 A1 | 9/2006 | Hines |
| 2006/0206199 A1 | 9/2006 | Churchwell et al. |
| 2006/0247680 A1 | 11/2006 | Amplatz et al. |
| 2006/0259131 A1 | 11/2006 | Molaei et al. |
| 2006/0264905 A1 | 11/2006 | Eskridge et al. |
| 2006/0264907 A1 | 11/2006 | Eskridge et al. |
| 2007/0067015 A1 | 3/2007 | Jones et al. |
| 2007/0088387 A1 | 4/2007 | Eskridge et al. |
| 2007/0106311 A1 | 5/2007 | Wallace et al. |
| 2007/0191884 A1 | 8/2007 | Eskridge et al. |
| 2007/0198075 A1 | 8/2007 | Levy |
| 2007/0203567 A1 | 8/2007 | Levy |
| 2007/0270902 A1 | 11/2007 | Slazas et al. |
| 2008/0004653 A1 | 1/2008 | Sherman et al. |
| 2008/0004692 A1 | 1/2008 | Henson et al. |
| 2008/0039930 A1 | 2/2008 | Jones et al. |
| 2008/0147100 A1 | 6/2008 | Wallace |
| 2008/0183143 A1 | 7/2008 | Palasis et al. |
| 2008/0221600 A1 | 9/2008 | Dieck et al. |
| 2008/0269774 A1 | 10/2008 | Garcia et al. |
| 2008/0319533 A1 | 12/2008 | Lehe |
| 2009/0069880 A1 | 3/2009 | Vonderwalde et al. |
| 2009/0125053 A1 | 5/2009 | Ferrera et al. |
| 2009/0306678 A1 | 12/2009 | Hardert et al. |
| 2010/0023105 A1 | 1/2010 | Levy et al. |
| 2010/0063531 A1 | 3/2010 | Rudakov et al. |
| 2010/0094335 A1 | 4/2010 | Gerberding et al. |
| 2011/0022149 A1 | 1/2011 | Cox et al. |
| 2011/0270373 A1 | 11/2011 | Sampognaro et al. |
| 2012/0143237 A1 | 6/2012 | Cam et al. |
| 2012/0143317 A1 | 6/2012 | Cam et al. |
| 2012/0245674 A1 | 9/2012 | Molaei et al. |
| 2012/0290067 A1 | 11/2012 | Cam et al. |
| 2012/0296361 A1 | 11/2012 | Cam et al. |
| 2013/0090682 A1 | 4/2013 | Bachman et al. |
| 2013/0204290 A1 | 8/2013 | Clarke et al. |
| 2013/0268046 A1 | 10/2013 | Gerberding et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304109 A1 | 11/2013 | Abrams et al. |
| 2014/0052233 A1 | 2/2014 | Cox et al. |
| 2014/0058420 A1 | 2/2014 | Hannes et al. |
| 2014/0121752 A1 | 5/2014 | Losordo et al. |
| 2014/0128901 A1 | 5/2014 | Kang et al. |
| 2014/0142608 A1 | 5/2014 | Eskridge et al. |
| 2014/0180377 A1 | 6/2014 | Bose et al. |
| 2014/0236216 A1 | 8/2014 | Gerberding |
| 2015/0039015 A1 | 2/2015 | Gerberding |
| 2015/0142025 A1 | 5/2015 | Brandeis |
| 2015/0142042 A1 | 5/2015 | Cox |
| 2015/0142043 A1 | 5/2015 | Furey |
| 2015/0157329 A1 | 6/2015 | Rudakov et al. |
| 2015/0157331 A1 | 6/2015 | Levy et al. |
| 2015/0164512 A1 | 6/2015 | Chin et al. |
| 2015/0164665 A1 | 6/2015 | Cam et al. |
| 2015/0182361 A1 | 7/2015 | Ferrera et al. |
| 2015/0196305 A1 | 7/2015 | Meyer et al. |
| 2015/0216534 A1 | 8/2015 | Riina et al. |
| 2015/0245932 A1 | 9/2015 | Molaei et al. |
| 2015/0250628 A1 | 9/2015 | Monstadt et al. |
| 2015/0282962 A1 | 10/2015 | Strauss et al. |
| 2015/0327867 A1 | 11/2015 | Bachman et al. |
| 2015/0342612 A1 | 12/2015 | Wu et al. |
| 2016/0015395 A1 | 1/2016 | Molaei et al. |
| 2016/0015396 A1 | 1/2016 | Cox et al. |
| 2016/0030050 A1 | 2/2016 | Franano et al. |
| 2016/0038153 A1 | 2/2016 | Losordo et al. |
| 2016/0249936 A1 | 9/2016 | Clarke et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |

FOREIGN PATENT DOCUMENTS

| | | |
|---|---|---|
| CN | 1399531 | 2/2003 |
| DE | 102008028308 | 4/2009 |
| EP | 0820726 | 1/1998 |
| EP | 996372 | 5/2000 |
| EP | 1527753 | 5/2002 |

(56) References Cited

FOREIGN PATENT DOCUMENTS

| EP | 1269935 | 1/2003 |
|---|---|---|
| JP | 2001286478 | 10/2001 |
| JP | 2002516705 A | 6/2002 |
| JP | 2003512129 A | 4/2003 |
| JP | 2005522266 A | 7/2005 |
| WO | WO 1997/024978 | 7/1997 |
| WO | WO 1997/026939 | 7/1997 |
| WO | WO 1997/031672 | 9/1997 |
| WO | WO 1998/023227 | 6/1998 |
| WO | WO 1998/050102 | 11/1998 |
| WO | WO 1999/005977 | 2/1999 |
| WO | WO 1999/007294 | 2/1999 |
| WO | WO 1999/015225 | 4/1999 |
| WO | WO 2000/013593 | 3/2000 |
| WO | WO 2001/030266 | 5/2001 |
| WO | WO 2001/093782 | 12/2001 |
| WO | WO 2002/000139 | 1/2002 |
| WO | WO 2002/013899 | 2/2002 |
| WO | WO 2002/071977 | 9/2002 |
| WO | WO 2002/078777 | 10/2002 |
| WO | WO 2002/087690 | 11/2002 |
| WO | WO 2003/059176 | 7/2003 |
| WO | WO 2003/075793 | 9/2003 |
| WO | WO 2004/019790 | 3/2004 |
| WO | WO 2004/026149 | 4/2004 |
| WO | WO 2004/105599 | 12/2004 |
| WO | WO 2005/033409 | 4/2005 |
| WO | WO 2005/082279 | 9/2005 |
| WO | WO 2002/047851 | 4/2007 |
| WO | WO 2008/151204 | 12/2008 |
| WO | WO 2010/028314 | 3/2010 |
| WO | WO 2011/029063 | 3/2011 |
| WO | WO 2014/029835 | 2/2014 |
| WO | WO 2015/179377 | 11/2015 |

OTHER PUBLICATIONS

Cordis NeuroVascular, Inc.; "Prowler Select LP Microcatheter," Product Brochure; No. 155-5585; Miami Lakes, FL, USA (2004).
Cordis NeuroVascular, Inc.; "Prowler Select Plus Microcatheter," Product Brochure; No. 154-9877-1; Miami Lakes, FL, USA (2003).
Cordis NeuroVascular, Inc.; "Rapid Transit Microcatheter," Product Brochure; No. 152-7369-2; Miami Lakes, FL, USA (2003).
Gupta et al. SMST-2003: Proc. Intl. Conf. Shape Memory Superelastic Technol.; Pacific Grove, CA; p. 639; 2003.
Micrus Copr.; "Concurse 14 Microcatheter" Product Brochure; Sunnyvale, CA, USA.
Polytetraflouroethylene Implants, DermNet NZ, Nov. 11, 2005, 3 pages, <http://dermetnz.org/polytetrafluoroethylene.html>.

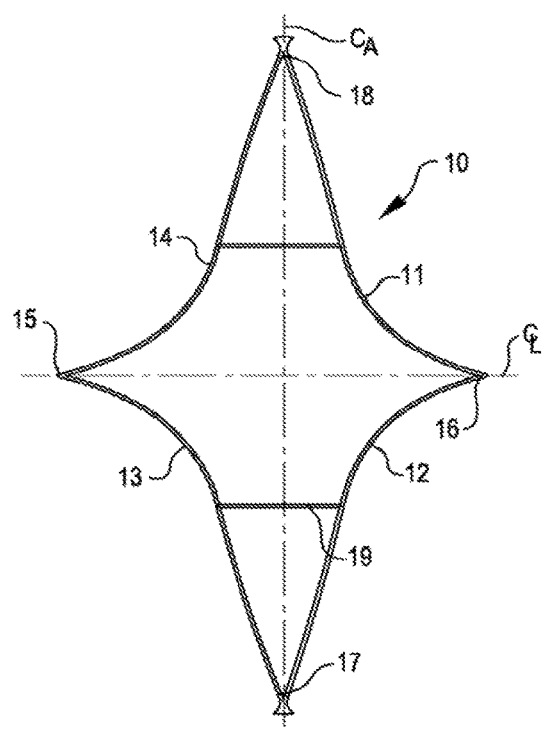
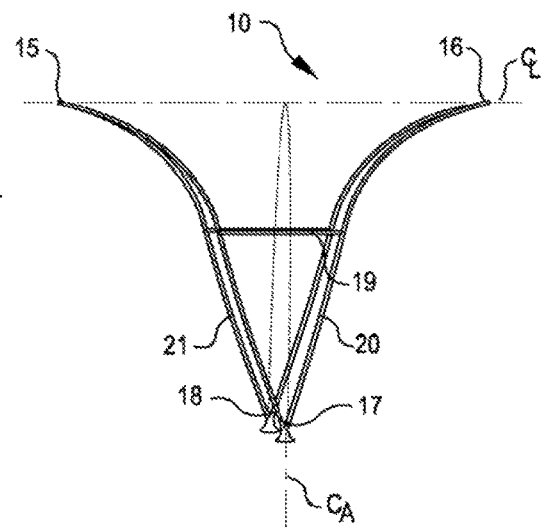
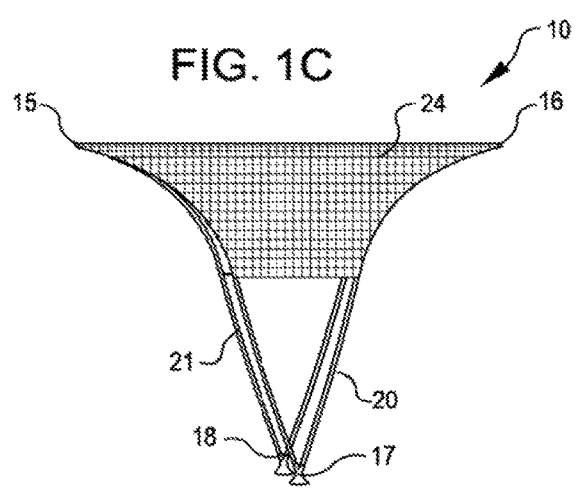

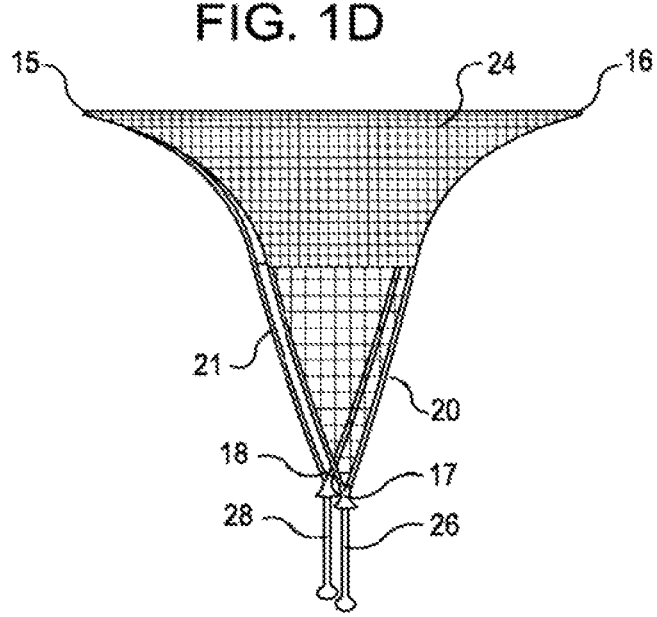
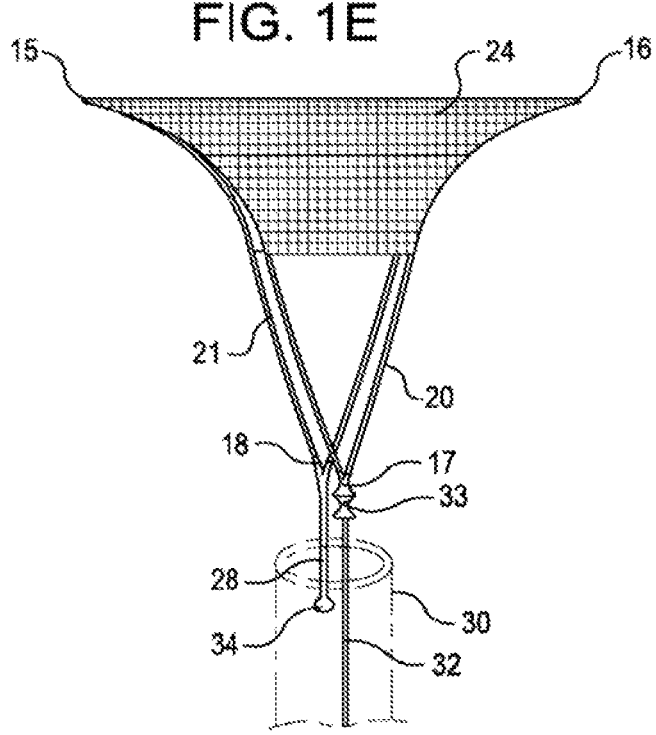

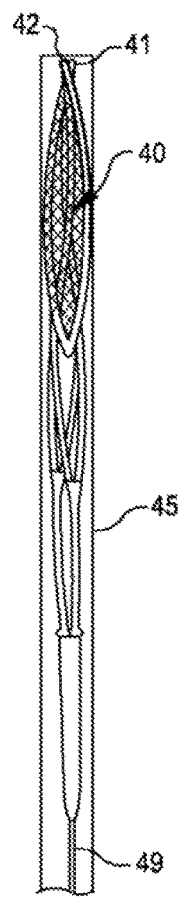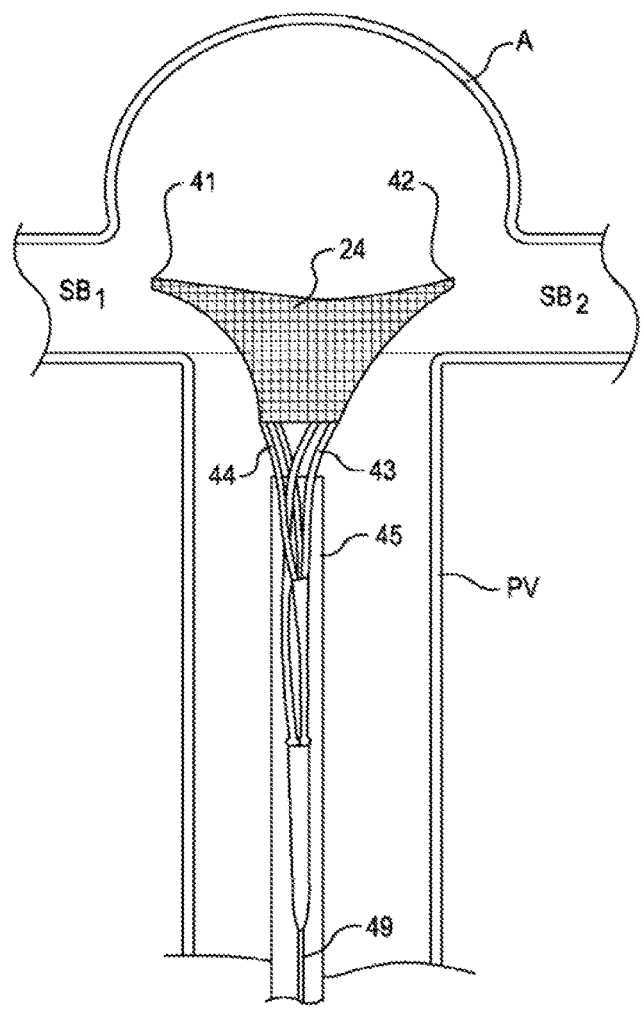

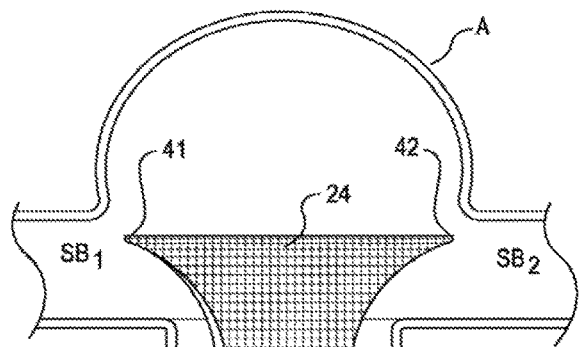
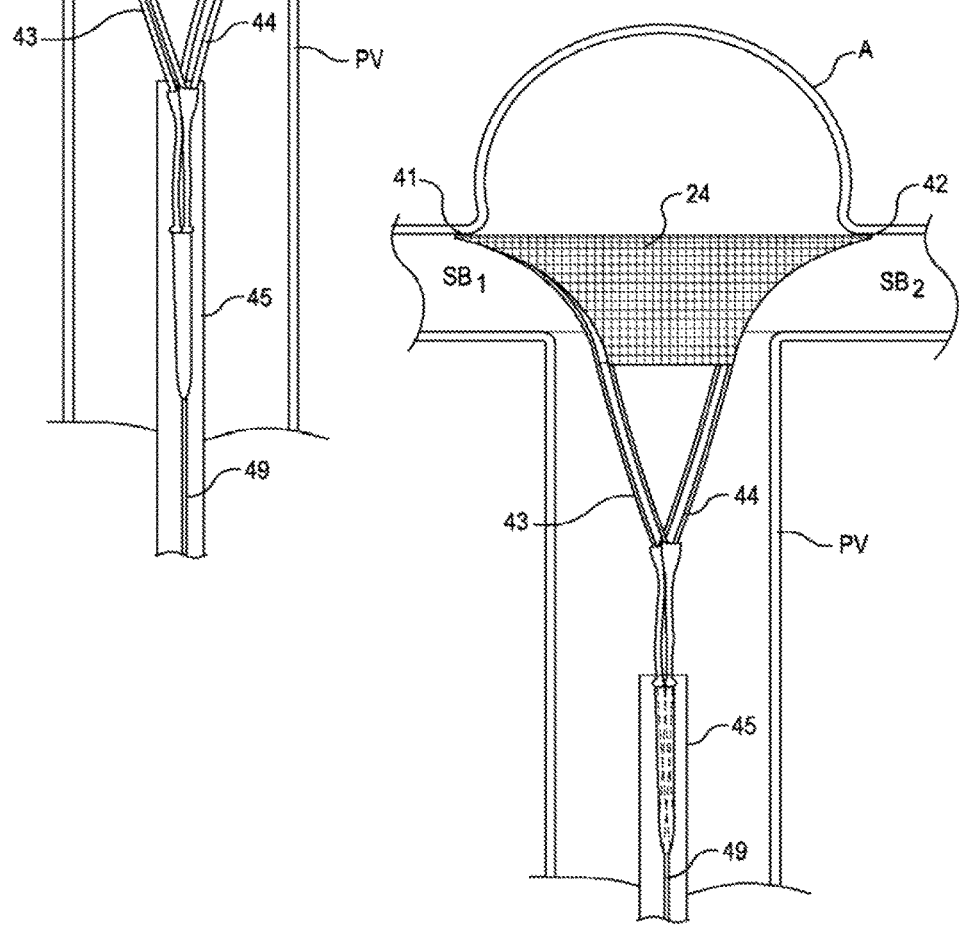

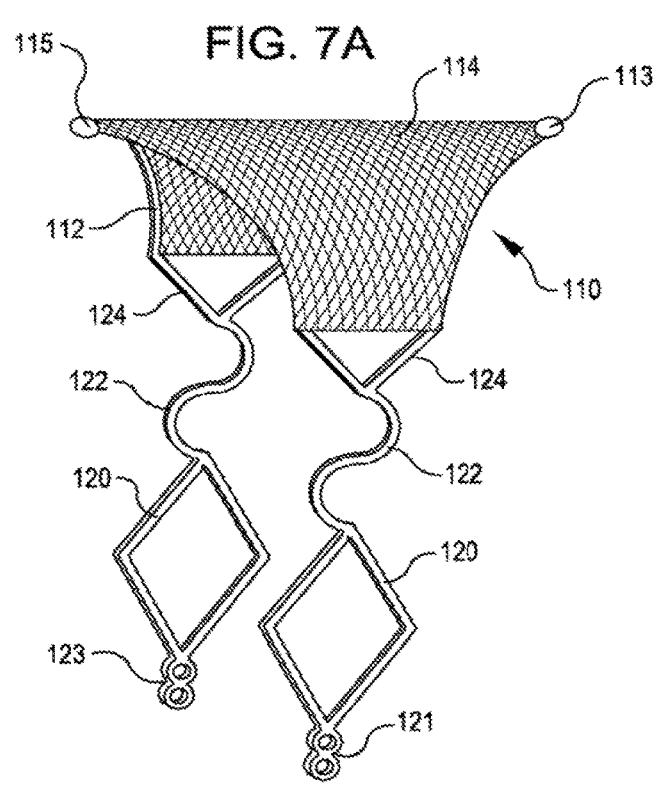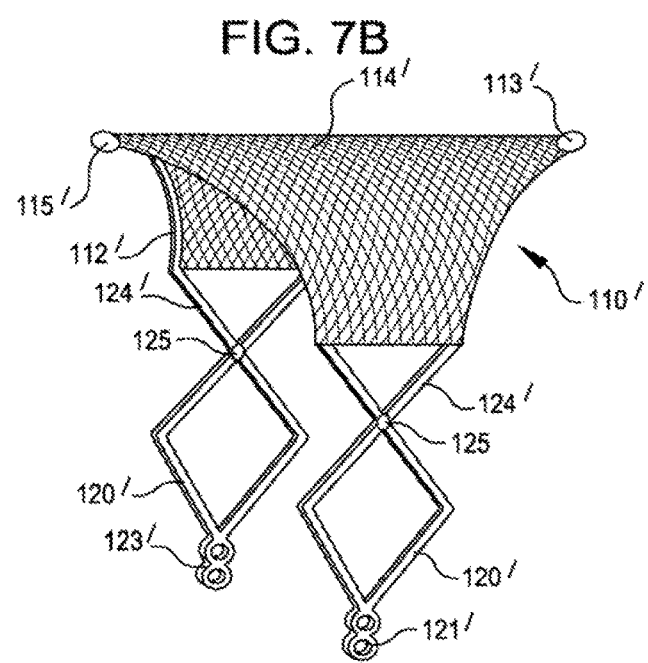

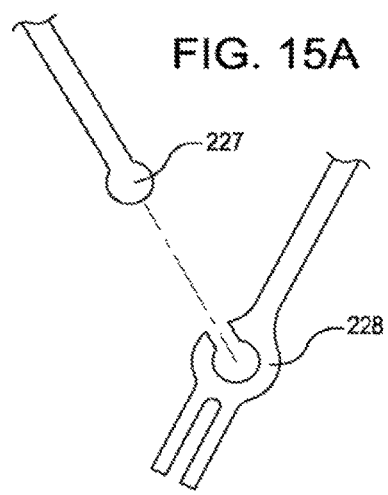
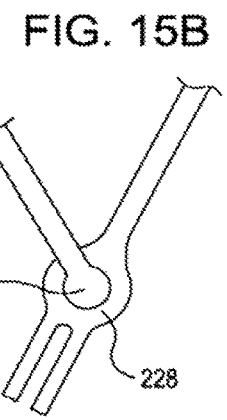
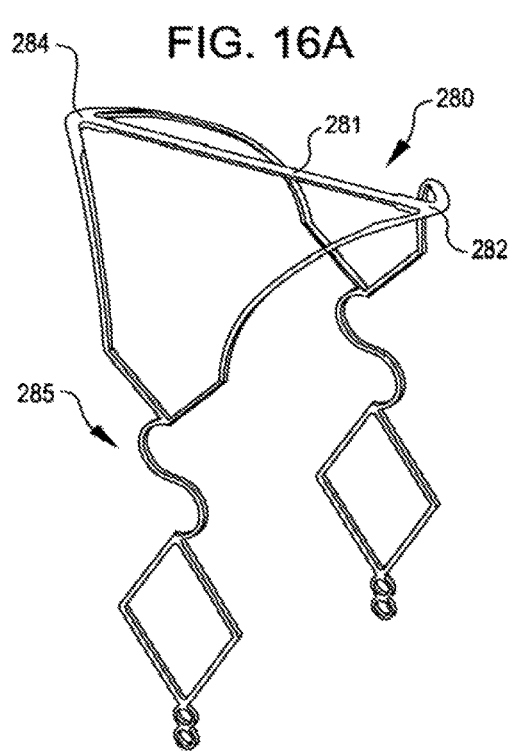
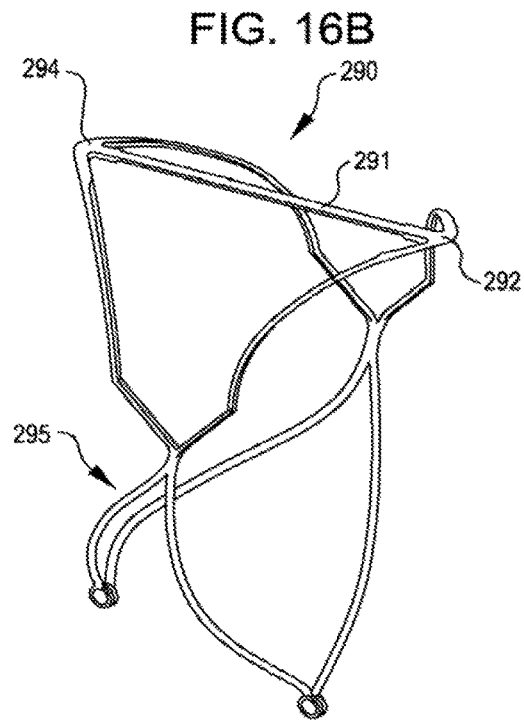

SYSTEMS AND METHODS FOR SUPPORTING OR OCCLUDING A PHYSIOLOGICAL OPENING OR CAVITY

CROSS-REFERENCE TO RELATED APPLICATIONS

This application is a continuation of U.S. patent application Ser. No. 14/618,969, filed on Feb. 10, 2015, which is a continuation of U.S. patent application Ser. No. 13/774,759 filed Feb. 22, 2013 (now U.S. Pat. No. 8,979,893 issued Mar. 17, 2015), which is a divisional of U.S. patent application Ser. No. 12/554,850 filed Sep. 4, 2009 (now U.S. Pat. No. 8,388,650 issued Mar. 5, 2013), which claims the benefit of priority of U.S. Application No. 61/094,693 filed Sep. 5, 2008, the content of which is incorporated herein by reference in its entirety.

TECHNICAL FIELD OF THE INVENTION

The present invention relates generally to implantable structures for placement in proximity to an opening or cavity in a physiological structure, such as the neck of an aneurysm, using minimally invasive techniques, and to methods of making and deploying such structures. In one aspect, the implantable structures described herein contact and support tissue in proximity to the opening or cavity. In another aspect, the implantable structures are at least partially occlusive and, when deployed across an opening in a physiological structure (e.g., aneurysm neck), provide flow diversion from the opening and may provide substantial occlusion of the opening. The structures described are particularly useful for placement at wide neck, terminal and bifurcation aneurysms.

BACKGROUND OF THE INVENTION

Surgical techniques for closing openings and repairing defects in anatomical lumens and tissues, such as blood vessels, septal defects and other types of physiological irregularities and defects, are highly invasive. Surgical methods for clipping aneurysms, for example, require opening the skull, cutting or removing overlying brain tissue, clipping and repairing the aneurysm from outside the blood vessel, and then reassembling tissue and closing the skull. Surgical techniques for repairing septal defects are also highly invasive. The risks associated with anesthesia, bleeding and infection during and following these types of procedure are high, and tissue that is affected during the procedure may or may not survive and continue functioning.

Minimally invasive surgical techniques may alternatively be used to place occlusive devices within or across an opening or cavity in the body, such as in the vasculature, spinal column, fallopian tubes, bile ducts, bronchial and other air passageways, and the like. In general, an implantable device is guided to a desired site through a delivery catheter and may be pushed through an opening at the distal end of the delivery catheter by a pusher mechanism, such as a pusher or delivery wire, thereby deploying the device at the desired site of intervention. Once the occlusive device has been placed at the desired location, it is detached from the pusher mechanism without disturbing placement of the occlusive device or damaging surrounding structures.

Aneurysms are bulges in an artery wall, generally caused by a weakening in the artery wall, that form an opening or cavity and are often the site of internal bleeding and stroke. In general, the minimally invasive therapeutic objective is to prevent material that collects or forms in the cavity from entering the bloodstream, and to prevent blood from entering and collecting in the aneurysm. This is often accomplished by introducing various materials and devices into the aneurysm.

Various types of embolic agents and devices are used to reduce risks to a patient associated with the presence of an aneurysm. One class of embolic agents includes injectable fluids or suspensions, such as microfibrillar collagen, various polymeric beads and polyvinylalcohol foam. These polymeric agents may be cross-linked (sometimes in vivo) to extend the persistence of the agent at the vascular site. These agents are often introduced into the vasculature through a catheter. After introduction and at the site, the introduced materials form a solid space-filling mass. Although some of these agents provide for excellent short term occlusion, many are thought to allow vessel recanalization due to absorption into the blood. Other materials, such as hog hair and suspensions of metal particles, have also been proposed and used to promote occlusion of aneurysms. Polymer resins, such as cyanoacrylates, are also employed as injectable vaso-occlusive materials. These resins are typically mixed with a radiopaque contrast material or are made radiopaque by the addition of a tantalum powder. Accurate and timely placement of these mixtures is crucial and very difficult. These materials are difficult or impossible to retrieve once they have been placed in the vasculature.

Implantable vaso-occlusive metallic structures are also well known and commonly used. Many vaso-occlusive devices are provided in the configuration of helical coils and are constructed from a shape memory material that forms a desired coil configuration upon exiting the distal end of a delivery catheter. The purpose of the coil is to fill the space formed by a defect or injury and facilitate formation of an embolus with the associated allied tissue. Multiple coils of the same or different structures may be implanted serially in a single aneurysm or other vessel defect during a procedure. Implantable framework structures are also used in an attempt to stabilize the wall of the aneurysm or defect prior to insertion of filling material such as coils.

Techniques for delivering a vaso-occlusive device to a target site generally involve a delivery catheter and a detachment mechanism that detaches the device, such as a coil, from a delivery mechanism after placement at the target sue. A microcatheter is initially steered through the delivery catheter into or adjacent to the entrance of an aneurysm, typically aided by the use of a steerable guidewire. The guidewire is then withdrawn from the microcatheter lumen and replaced by the implantable vaso-occlusive coil. The vaso-occlusive coil is advanced through and out of the microcatheter and thus deposited within the aneurysm or other vessel abnormality. Implantation of the vaso-occlusive device within the internal volume of a cavity and maintenance of the device within the internal volume of the aneurysm is crucial. Migration or projection of a vaso-occlusive device from the cavity may interfere with blood flow or nearby physiological structures and poses a serious health risk.

One type of aneurysm, commonly known as a "wide neck aneurysm" is known to present particular difficulty in the placement and retention of vaso-occlusive coils. Wide neck aneurysms are generally referred to as aneurysms of vessel walls having a neck or an entrance zone from the adjacent vessel that is large compared to the diameter of the aneurysm or that is clinically observed to be too wide to effectively retain vaso-occlusive coils deployed using the techniques discussed above.

The placement of coils, or other structures or materials, in the internal space of an aneurysm or other defect has not been entirely successful. The placement procedure may be arduous and lengthy, requiring the placement of multiple devices, such as coils, serially in the internal space of the aneurysm. Longer procedures, in general, involve higher risks of complication from anesthesia, bleeding, infection, and the like. Moreover, because placement of structures in the internal space of an aneurysm doesn't generally completely occlude the opening, recanalization of the original aneurysm is more likely to occur, debris and occlusive material may escape from within the aneurysm and present a risk of stroke, vessel blockage or other undesirable complications. Blood may also flow into aneurysm and other blood vessel irregularities after the placement of embolic devices, which increases the risks of complication and further enlargement of the aneurysm. Furthermore, some aneurysms, vessels and other passageway defects are not well-suited to placement of coils or other conventional occlusive devices.

Devices for maintaining vaso-occlusive coils within an aneurysm nave been proposed. One such device is described in U.S. Pat. No. 5,980,514, which discloses devices that are placed within the lumen of a feed vessel exterior to the aneurysm to retain coils within the aneurysm cavity. The device is held in place by means of radial pressure of the vessel wall. After the device is released and set in an appropriate place, a microcatheter is inserted into the lumen behind the retainer device and the distal end of the catheter is inserted into the aneurysm cavity for placement of one or more vaso-occlusive devices. The retainer device prevents migration of occlusive devices from the cavity. A removable occlusion system for covering the neck of an aneurysm while embolic material is delivered to the aneurysm is described in U.S. Pat. No. 5,928,260.

Another methodology for closing an aneurysm is described in U.S. Pat. No. 5,749,894, in which a vaso-occlusive device, such as a coil or braid, has on its outer surface a polymeric composition that reforms or solidifies in situ to provide a barrier. The polymer may be activated, e.g. by the application of light, to melt or otherwise to reform the polymer exterior to the vaso-occlusive device. The vaso-occlusive device then sticks to itself at its various sites of contact and forms a rigid whole mass within the aneurysm.

Devices for bridging the neck of an aneurysm have also been proposed. U.S. Patent Application Publication No. 2003/0171739 A1, for example, discloses a neck bridge having one or more array elements attached to a junction region and a cover attached to the junction region and/or the array elements. The array elements may comprise Nitinol alloy loops and the cover may comprise a fabric, mesh or other sheeting structure.

U.S. Patent Application Publication No. 2004/0087998 A1 discloses a device and method for treatment of a vascular defect in which two sheets, or a sheet and a strut structure function to secure the vaso-occlusive device and to occlude an opening. This patent publication lists numerous biocompatible compositions and materials that may be used in connection with the device to promote adhesion, fibrosis, tissue growth, endothelialization or cell growth.

U.S. Patent Application Publication No. 2004/0193206 A1 discloses another device for at least partially occluding an aneurysm including a plurality of elongate members configured to move relative to one another to transform the bridge between the delivery and deployed configurations. A two array bridge, in which a first array is deployed inside the aneurysm and a second array is deployed outside the aneurysm is also disclosed.

U.S. Patent Application Publication Nos. 2007/0088387 A1 and 2007/01918844 A1 disclose methods and systems for repairing defects in physiological lumens, such as aneurysms by placing occlusive devices having closure structures covering the opening, when deployed, and anchoring structures contacting the inner aneurysm wall, or the parent vessel, or both.

Septal defect closure devices are also well known. Such devices occlude openings, or septal defects, in the heart or the vascular system. Septal closure devices are disclosed, for example, in U.S. Pat. Nos. 6,077,291 and 6,911,037. Bronchial flow control devices that seal or partially seal a bronchial lumen are also known, see, e.g., U.S. Pat. No. 7,011,094.

Systems currently used for the detachment of implantable devices after placement include mechanical systems, electrolytic systems and hydraulic systems. In mechanical systems, the occlusive device and the pusher wire are linked by means of a mechanical joint, or inter-locking linkage, which separates once the device exits the delivery catheter, thereby releasing the device. Examples of mechanical systems include those taught in U.S. Pat. Nos. 5,263,964, 5,304,195, 5,350,397, and 5,261,916. In electrolytic systems, a constructed joint (generally either fiber- or glue-based) connects the pusher wire to the occlusive device and, once the device has been placed in the desired position, the joint is electrolytically disintegrated by the application of a current or heat. An example of an electrolytic system is provided in U.S. Pat. No. 5,624,449. In hydraulic systems, the pushing wire is connected to the occlusive device by means of a polymer coupling. The pushing wire contains a micro-lumen to which the physician attaches a hydraulic syringe and, upon the application of pressure using the syringe plunger, the hydraulic pressure forces the polymer joint to swell and break, thereby releasing the device. An example of a hydraulic system is described in U.S. Pat. No. 6,689,141.

Despite the numerous devices and systems available for placing embolic materials in an aneurysm and for occluding physiological defects using minimally invasive techniques, these procedures remain risky and the results rarely restore the physiological structure to its normal, healthy condition. Challenges also remain in accurate positioning of implantable devices during deployment, preventing shifting or migration of implantable devices following deployment, and preserving flow in neighboring vessels following placement of implantable devices. Methods and systems of the present invention are directed, among other things, to reducing the length and complexity of minimally invasive procedures for supporting and occluding openings and repairing a lumen or tissue defect, and to restoring a physiological structure, such as a blood vessel, to its normal, healthy condition. Methods and systems of the present invention are additionally directed to providing implantable devices for supporting and/or at least partially occluding an opening or cavity, such as an aneurysm, that are safely and conveniently deployable using minimally invasive techniques, that reduce shifting and migration following placement, and that do not restrict blood flow in neighboring vessels following deployment.

SUMMARY

The present invention provides methods and systems for placing and anchoring an implantable structure at an opening in an internal lumen or cavity within a subject's body using minimally invasive techniques. In general, these systems and methods are used in connection with vascular abnormalities such as openings or cavities and are described herein with reference to their application to aneurysms and other types of blood vessel defects. It will be appreciated, however, that systems and methods of the present invention are not limited to these applications and may be employed in a variety of medical indications in which placement of structures at an opening or cavity in a physiological lumen or passageway or tissue is desired.

The implantable devices described herein are suitable for placement at a cavity or opening that faces or is accessible from a neighboring lumen or passageway through which an implantable device may be delivered and deployed, such as at the neck of a wide neck, terminal or bifurcation aneurysm. The implantable devices have a generally inverted U-shaped profile with a curved or angled framework support structure sized and configured for placement in proximity to, and generally contacting, the tissue surrounding the opening or cavity, such as the neck of the aneurysm. The implantable devices additionally comprise at least two anchoring legs extending (proximally) from the framework structure sized and configured to contact the wall of a lumen, such as a neighboring blood vessel, that extends proximally from the opening. The anchoring legs are generally sized and configured to extend for a distance proximally along the lumen (e.g., parent vessel) sufficient to anchor proximal to the margins of the aneurysm. This is an important feature, because some aneurysms may fully encompass the lumen, rather than protruding from a radial section of the lumen.

Endoluminal and endovascular procedures are commonly used for placing implantable devices and materials in many types of interventions. An intravascular guide catheter is generally inserted into a patient's vasculature, such as through the femoral artery, and guided through the vasculature to, or approaching, a desired site of intervention. Additional delivery mechanisms and specialized catheters, such as microcatheters, pusher devices and the like, may be used to facilitate delivery of various devices and accessories to the target site. Implantable devices are generally detachably mounted to a pusher or delivery mechanism and navigated through the guide catheter to the target site, where they are deployed and detached from the delivery mechanism. The delivery mechanism is then withdrawn through the guide catheter and additional devices, accessories, drugs or the like may be delivered to the target site, if desired, prior to removal of the guide catheter.

In general, implantable devices of the present invention are delivered to a target site, such as in the neurovasculature, in a small diameter, constrained condition. In one aspect, the present invention provides implantable device assemblies comprising an elongated, flexible delivery catheter, at least one elongated, flexible delivery mechanism axially movable with respect to the catheter, and an implantable device in a small diameter, constrained condition associated with a distal end of the delivery mechanism and mounted at or near a distal end of the delivery catheter. The delivery mechanism may be a delivery (or pusher) wire or tube and may be detachably bonded to the implantable device at or near its distal end. In alternative embodiments, the delivery mechanism may be an expandable or inflatable device, such as a balloon that facilitates placement and/or expansion of the implantable device during deployment.

In another embodiment, the implantable device may be associated with a distal end of a delivery mechanism, such as a delivery wire, or multiple delivery wires, and an elongated, flexible introducer sheath provided over the delivery wire(s) and sized and configured for passage through a guiding catheter or a delivery catheter. The implantable device may be stored in a small diameter, delivery condition within a distal end of the sheath. In alternative embodiments, the implantable device may be assembled and stored in an expanded, deployed condition in a protective container, with a proximal end of the implantable device attached to the delivery mechanism with the introducer sheath mounted over the delivery mechanism. In this embodiment, the implantable device is provided in a delivery condition by retracting the device into the distal end of the sheath prior to use.

The assembly is designed to be compatible with standard marketed endovascular delivery system technologies and can be loaded at the proximal catheter hub and then advanced the distance of the (already placed) guiding or delivery catheter, exiting the delivery catheter at the target deployment site. Upon proper positioning at the target deployment site, the implantable device is advanced out of the restraining device in a controllable fashion and, as it exits the restraining device, the device assumes its larger diameter deployed condition as it is positioned at the site. The device may be advanced using one or more delivery wire(s) electrolytically, mechanically, hydraulically and/or thermally attached to the device and can be separated from the device using electrolytic, mechanical, hydraulic and/or thermal techniques. Alternatively, the device may be advanced or deployed using a pusher or a push/pull technique that requires no mechanical, hydraulic, thermal or electrolytic attachment method. A pusher may act as a pusher and/or a stabilizer for deployment of the device. The device may be partially or fully deployed, and detached or not, depending on the application.

In the larger diameter deployed condition, implantable devices of the present invention comprise a generally inverted U-shaped, curved or angular framework support structure and at least two anchoring legs extending from the inverted U-shaped support structure along substantially opposed planes. The inverted U-shaped support structure is sized and configured for placement across the neck of an aneurysm and generally has a perimeter structure having a largest dimension at least as large as the dimension of the aneurysm neck. The anchoring legs are sized and configured to extend proximally from the support structure and the aneurysm neck following placement and deployment and contact the walls of a neighboring vessel at generally opposed locations. In some embodiments, the anchoring legs extend from the framework support structure along substantially aligned, spaced apart planes. In some embodiments, implantable devices of the present invention comprise anchoring legs having a multi-dimensional configuration and, in a deployed condition, contact walls of a neighboring vessel at multiple, generally opposed locations.

In some embodiments, the framework structure forms a perimeter structure for supporting an occlusive or semi-occlusive cover, or membrane, designed to restrict or inhibit flow into the cavity or escape of materials from the cavity. In this aspect, methods and systems of the present invention may provide repair and reconstruction of a lumen, such as a blood vessel, by placement and retention of a closure structure across an opening or cavity to exclude the opening (e.g., aneurysm) from the parent artery and to divert blood flow away from the opening. Following placement and deployment, the closure structure may substantially cover the opening or cavity and form a structure that substantially conforms to the tissue surrounding the opening and/or the neighboring lumen wall to restore the lumen to the configuration it would assume in its healthy condition. Neither the anchoring structures, nor the support structure, nor the membrane interferes substantially with normal or desired fluid flow in the lumens in proximity to the opening.

Coverings and membranes including both occlusive and semi-occlusive materials may be provided and supported by the framework structure. Occlusive and semi-occlusive coverings and membranes may incorporate pores or perforations and may have a variety of surface treatments. They may incorporate or be associated with a variety of materials to provide properties desired for various applications. The inverted U-shaped framework structure is generally sized and configured to reside entirely outside the neck of the aneurysm following deployment. In some embodiments, the framework support structure may be associated with a structure extending distally for placement inside the aneurysm.

At least two anchoring legs extend from the inverted U-shaped framework structure and, when deployed, contact the walls of a neighboring passageway, such as the walls of the parent vessel of a terminal or bifurcation aneurysm with enough purchase to clear the aneurysm margin at substantially opposed locations. The anchoring structures are generally atraumatic and maintain the U-shaped framework structure in position across the opening without damaging the neighboring tissue or restricting blood flow neighboring vessel(s) or tissue. In a deployed condition, the anchoring leg(s) extend proximally from the opening and the framework structure and contact the wall of a lumen terminating in the opening, such as a parent vessel. The anchoring legs thus support the framework structure and maintain it in position across the opening without occluding any bifurcating lumens or vessels and without occluding the lumen terminating in the opening, such as the parent vessel.

The anchoring legs are generally formed integrally with or bonded to the inverted U-shaped framework support structure and extend proximally from the framework support structure when deployed, substantially opposite one another. In some embodiments, the anchoring legs are symmetrical and each anchoring leg has substantially the same configuration. In alternative embodiments, the anchoring legs may have different configurations, sizes, or the like. In one embodiment, the legs have a generally tapered configuration, with a wider contact profile in the area near the curved framework structure and a narrower contact profile as the legs extending proximally. In some embodiments, the anchoring legs may form substantially planar structures aligned on substantially opposed, spaced apart planes. In other embodiments, the anchoring legs may have a curved configuration that corresponds generally to the curved configuration of the vessel wall and, following deployment, the anchoring legs are aligned substantially opposite one another contacting the vessel wall.

In another embodiment, the anchoring legs, when deployed, extend proximally from the framework structure opposite one another to contact the vessel wall in two opposed regions and additionally incorporate proximal extensions that extend away from the anchoring legs and terminate at locations where they contact the vessel wall in two different opposed regions. The proximal extensions provide additional support and additional vessel wall surface area contact for the implantable device following deployment. In one embodiment, the distal extensions of the anchoring legs are formed by joining distal segments extending from opposed anchoring legs together at a circumferential location intermediate the circumferential locations of the terminal ends of the anchoring legs. Anchoring legs incorporating proximal extensions provide at least four disparate circumferential vessel contact areas, arranged as two sets of generally opposed vessel contact areas at different areas along the parent vessel. In one embodiment, the anchoring legs contact the parent vessel along contact areas substantially opposite one another and the proximal extensions contact the parent vessel along contact areas substantially opposite one another and proximal to and rotated approximately 90.degree. from the anchoring leg contact areas.

Various agents, such as agents that promote re-endothelialization and tissue growth, as well as bonding agents, therapeutic agents, anti-thrombolytic agents, hydrophilic and/or hydrophobic agents, and the like may be provided to the site during or following the placement procedure and/or in association with the implantable device of the present invention. Exemplary agents that may be administered prior to, during or subsequent to device deployment, or may be associated with the implantable device, are disclosed in U.S. Patent Application Publication Nos. 2004/087998 A1, 2004/0193206 A1 and 2007/0191884 A1, which are incorporated by reference herein in their entireties. It will also be appreciated that radiopaque markers or radiopaque compounds may be associated with certain structures or portions of the implantable device and delivery assembly structure to facilitate accurate positioning, placement and monitoring of the device during and following deployment.

In one aspect, methods and systems of the present invention provide exclusion of a defect, such as an aneurysm, and diversion of blood flow away from the aneurysm by placement of a framework structure incorporating a membrane that restricts access to and restricts or prevents flow communication between the vessel and the interior of the aneurysm across the neck of the aneurysm, and retention of the framework structure and membrane across the opening by means of one or more anchoring structures extending from the framework structure proximally and contacting walls of a neighboring vessel, such as a parent vessel, in generally opposed regions. Methods and systems of the present invention may further promote shrinking and reabsorption of the defect, or portions of the defect, and facilitate hemostasis inside the defect. In one aspect, methods and systems of the present invention not only restore the structure and function of the parent vessel in the vicinity of the defect, but also stabilize material inside the aneurysm, prevent debris from escaping into the bloodstream, and promote a reduction in the size and mass of the aneurysm.

In some embodiments in which the implantable device that incorporates an occlusive or semi-occlusive cover associated with the framework structure, systems and methods of the present invention are directed to providing flow diversion and exclusion/occlusion of the cavity, such as an aneurysm, in a bifurcation or terminal aneurysm situation. In some embodiments, the implantable device may be utilized in combination with adjunctive devices such as endovascular helically wound coils, liquid embolic glues, stents and other agents that are deployed in a cavity or aneurysm prior to, during or following placement of the implantable device across the neck of the aneurysm. In these embodiments, the implantable device may function to retain adjunctive devices within the cavity and may, optionally, also provide flow diversion from and occlusion of the cavity.

BRIEF DESCRIPTION OF THE DRAWINGS

FIG. 1A shows a plan view of an implantable device of the present invention in a substantially flat, preassembled configuration.

FIG. 1B shows a schematic side perspective view of the implantable device of FIG. 1A in a folded, assembled configuration.

FIG. 1C shows a schematic side perspective view of an implantable device of the present invention incorporating a curved framework structure supporting a cover and anchoring legs extending to form an implantable device having a generally inverted U-shaped profile.

FIG. 1D shows a schematic side perspective view of an implantable device of the present invention similar to the device shown in FIG. 1C but having a different anchoring leg structure.

FIG. 1E shows a schematic side perspective view of an implantable device of the present invention similar to the devices shown in FIGS. 1C and 1D but having a different anchoring leg structure.

FIGS. 2A-2F show schematic Side perspective views of an implantable device having a configuration similar to that of the device illustrated in FIG. 1B in a small diameter delivery condition within a delivery catheter (FIG. 2A), in various stages of deployment from the delivery catheter at the site of a terminal aneurysm (FIGS. 2B-2D) and, detached from the delivery mechanism(s) and in place across the neck of the terminal aneurysm (FIGS. 2E,2F).

FIGS. 7A and 7B show schematic side perspective views of alternative embodiments of an implantable device of the present invention having an alternative anchoring leg configurations providing flexing of the framework support structure with respect to proximal anchoring legs.

FIG. 12A shows a plan view of a device of the present invention in a substantially flat, pre-assembled form. FIG. 12B shows a side perspective view of the pre-assembled device of FIG. 12A in an assembled form. FIG. 12C shows a front cut-away view of the implantable device of FIG. 12B deployed across the neck of an aneurysm, and FIG. 12D shows a side perspective cut-away view of the implantable device of FIG. 12B deployed across the neck of an aneurysm.

FIGS. 15A and 15B show enlarged schematic plan views of anchoring leg terminal portions having mating configurations.

FIG. 16A shows a side perspective view of an implantable device of the present invention comprising a framework structure and anchoring legs without a cover membrane, and FIG. 16B shows a side perspective view of an implantable device having a framework structure similar to that shown in FIG. 16A with anchoring legs having a different configuration.

Figure 2E:
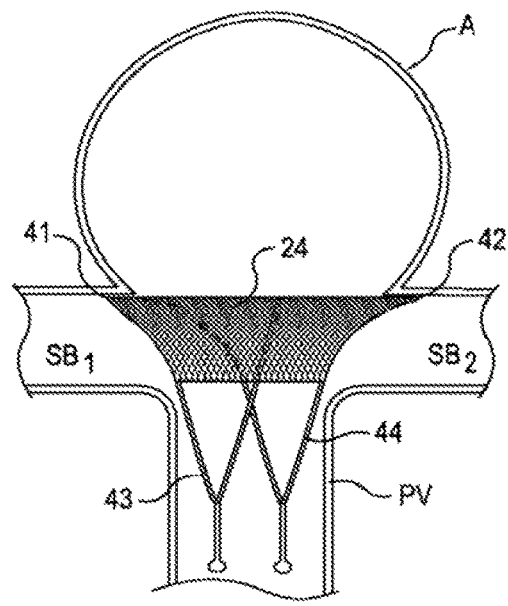

Like numbers have been used to designate like pares throughout the various drawings to provide a clear understanding of the relationship of the various components and features, even though different views are shown. It will be understood that the appended drawings are not necessarily to scale, and that they present a simplified, schematic view of many aspects of systems and components of the present invention. Specific design features, including dimensions, orientations, locations and configurations of various illustrated components may be modified, for example, for use in various intended applications and environments.

DETAILED DESCRIPTION

In general, implantable assemblies of the present invention comprise an implantable device attached to at least one delivery wire or tube and loaded in a catheter or a sheath for delivery to a target site in a human body, such as in the neurovasculature at a site in proximity to a wide mouth, termination or bifurcation aneurysm. The implantable device is delivered to the target site in a small diameter, constrained condition and is deployed, at the site, to its larger diameter deployed condition. The device, in the deployed condition, comprises a generally inverted U-shaped three-dimensional framework support structure having a perimeter structure configured to be positioned in close proximity to, and generally contacting tissue at the neck of the aneurysm along at least a portion of its perimeter.

The framework support perimeter structure may incorporate substantially opposed lateral corners, or wing tip structures, lying on a longitudinal centerline of the framework support structure that, when positioned across the neck of an aneurysm, contact substantially opposed portions of the aneurysm neck, or the vessel wall in proximity to the aneurysm, to support the opening. The generally U-shaped portions of the framework structure extending on either side of a longitudinal centerline and between the lateral corners may be configured to contact portions of the neck of the aneurysm or circumferential areas of the vessel wall in proximity to the neck of the aneurysm when positioned across the neck of an aneurysm. This implantable device configuration, when deployed, supports the neck of the aneurysm (and/or neighboring vessel wall surface area) at lateral corners of the device and additionally supports the neck of the aneurysm (and/or neighboring vessel wall surface area) in radial, or circumferential, surface areas located between lateral corner supports.

An occlusive or semi-occlusive closure structure, such as a mesh structure or a membrane, may be associated with the framework support structure to at least partially occlude the opening following placement. The closure structure, like the perimeter structure, may additionally extend circumferentially on either side of and away from a longitudinal centerline, and between the lateral corners, to contact portions of the neck of the aneurysm or radial or circumferential areas of the aneurysm neck and/or between the areas of wing tip contact. The closure structure may fully or partially extend over the neck of an aneurysm following deployment.

The implantable device additionally comprises at least two discrete anchoring legs extending proximally from the framework support structure that, in a three-dimensional deployed profile, form the terminal legs of the inverted U-shaped structure. The anchoring legs are configured to contact the wall of a neighboring vessel, such as the parent vessel, following placement and deployment of the framework support structure across the neck of an aneurysm. Several specific embodiments of implantable devices incorporating inverted U-shaped framework support structures and having at least two anchoring legs extending from proximal regions of the framework structure are described with reference to the figures.

The implantable device embodiments described in detail below are intended to be exemplary rather than limiting in nature. It is intended that component parts, structures and materials of construction described herein with respect to specific embodiments may be used in connection with other embodiments incorporating other components and functionalities, as desired, to provide devices having appropriate configurations and functionalities for various and disparate applications. A person having ordinary skill in the art will appreciate how various of the components and structures herein may be combined to provide yet additional devices and functionalities.

FIGS. 1A and 1B schematically illustrate an implantable device 10 of the present invention in a substantially flat, pre-assembled configuration (FIG. 1A) and in a three-dimensional deployed configuration (FIG. 1B). As shown, in FIG. 1A, implantable device 10 comprises a framework structure having a generally diamond-shaped configuration formed by framework sides 11, 12, 13 and 14. In preferred embodiments, framework sides 11, 12, 13 and 14 are joined at corners 15, 16, 17, 18, with longitudinal centerline CL extending between lateral corners 15 and 16 and axial centerline CA extending between axial corners 17 and 18. Framework sides 11, 12, 13 and 14, in the embodiment illustrated in FIGS. 1A-1E, form a perimeter structure and curve inwardly toward axial centerline CA in the area near the longitudinal centerline CL In the embodiment illustrated in FIGS. 1A and 1B, implantable device 10 is generally symmetrical with respect to both the longitudinal and axial centerlines CL and CA. In alternative embodiments, implantable device 10 may have an asymmetrical configuration with respect to either the longitudinal or axial centerlines, or both.

While corners 15, 16, 17 and 18 are illustrated as being pointed, it will be appreciated that the corners may have a curved profile, or a more complex curved or angular configuration. Framework sides 11, 12, 13 and 14 may be formed integrally with one another, or separate framework sides may be provided and bonded to one another at the corners. In one embodiment, the implantable device framework structure is constructed from a substantially flat substrate by cutting, etching (or otherwise) the framework shape from a substantially flat substrate sheet. The framework structure and anchoring legs may be constructed from material having a substantially uniform thickness or, in alternative embodiments, the thickness of the framework structure and/or anchoring legs may vary. In one embodiment, for example, the thickness of the anchoring legs may be greater in regions near their proximal terminus or junction.

Implantable device 10 may be assembled from the pre-assembled form of FIG. 1A to the assembled form shown in FIG. 1B simply by bringing axial corners 17 and 18, located on axial centerline CA, toward one another and forming a substantially inverted U-shaped framework structure with the lateral corners 15, 16 located on longitudinal centerline CL positioned at the "top" of the inverted U-shaped support structure in the views shown in FIGS. 18-1E, which is oriented distally during and following deployment of the device. The longitudinal centerline CL is positioned substantially at the midline of the curved portion of the inverted U-shaped structure, while the axial centerline CA generally bisects the device and joins axial corners 17, 18 forming the terminal ends of the implantable device.

In this assembled configuration, implantable device 10 comprises a framework support having a perimeter structure formed by the framework sides extending medially and radially from both lateral corners 15 and 16 for some distance, such as to lateral marker 19, forming an inverted U-shaped structure when viewed from the end. The framework support structure is positioned distally during deployment, with at least a portion of the perimeter structure designed and configured to be positioned in proximity to, and generally contact and support tissue in proximity to an opening or cavity such as an aneurysm. In particular, the framework support structure in proximity to lateral corners 15, 16 aligned on longitudinal centerline CL may provide contact points for contacting the neck of an aneurysm or a vessel wall in proximity to the neck of an aneurysm during and following deployment of the implantable device. In some embodiments, wingtip extensions may be provided projecting along the longitudinal centerline from the lateral corners to extend the reach of the framework support structure. The side walls extending proximally and medially from longitudinal centerline CL may contact the neck of the aneurysm and/or the vessel wall medially and circumferentially in the areas between the locations where the lateral corners and/or the wingtip extensions contact the vessel wall.

Anchoring legs 20, 21 extend (proximally) away from the curved framework support, forming the legs of the inverted U-shaped structure and, in the embodiment illustrated in FIG. 1B, form generally triangular structures arranged substantially parallel to one another and spaced a distance from one another. Anchoring legs 20, 21 are generally atraumatic to tissue and contact the vessel walls over an extended surface area. Following deployment, the corners 15, 16 of the framework support structure in proximity to the longitudinal centerline CL form wingtip extensions that are positioned distally across the neck of an aneurysm, while the anchoring legs are positioned proximally to contact and be supported by walls of a neighboring vessel in proximity to the neck of the aneurysm, such as a parent vessel. This arrangement provides stable positioning of the device across the neck of an aneurysm or another opening and reduces the possibility of device migration without interfering with now in the associated and neighboring vessels.

FIG. 1C shows another embodiment of a generally inverted U-shaped framework structure having a configuration similar to that shown in FIG. 1B but having an occlusive or semi-occlusive closure membrane 24 associated with the substantially inverted U-shaped framework structure. In the embodiment illustrated in FIG. 1C, occlusive membrane 24 is substantially co-extensive with the framework perimeter structure in the region of and extending for some distance on both sides of longitudinal centerline CL. Anchoring legs 20, 21 extend away from the framework support structure and occlusive membrane 24, aligned substantially opposite one another. In the embodiment illustrated in FIG. 1C, anchoring legs 20, 21 are substantially planar structures and are aligned on substantially parallel, opposed planes. In alternative embodiments, anchoring legs 20, 21 may be provided as curved structures aligned substantially opposite one another and curving generally symmetrically with respect to the axial centerline CA, generally matching the curvature of a lumen or vessel. In yet alternative embodiments, more than two discrete anchoring legs may be provided extending proximally from the framework support structure in a generally radially symmetrical arrangement, providing multiple surfaces for contacting multiple regions of the parent vessel.

Closure membrane 24 is generally designed to at least partially cover an opening such as an aneurysm neck and may have an irregular but symmetrical configuration, as shown. Closure membrane 24 may completely block flow into or out from an aneurysm, or it may partially block flow when it has a porous or perforated structure or is constructed from a permeable material or covers a surface area smaller than that of the aneurysm neck.

FIG. 1D shows another embodiment of a generally inverted U-shaped framework structure having a configuration similar to that shown in FIG. 1B, having an occlusive or semi-occlusive closure membrane 24 as shown in FIG. 1C, and also having anchoring leg extensions 26, 28. Anchoring leg extensions 26, 28 are formed integrally with or bonded to the corners 17, 18, respectively, forming the terminal ends of anchoring legs 20, 21. Anchoring leg extensions 26, 28 have a configuration different from anchoring legs 20, 21 and may be simple linear extensions, as shown in FIG. 1D, or may take more complex configurations. Anchoring leg extensions 26, 28 are generally aligned substantially on the plane of the associated anchoring leg. In the embodiment shown in FIG. 1D, anchoring legs 20, 21 are associated with a porous or fibrous matrix material that is provided in openings in anchoring legs 20, 21 and promotes contact with and/or anchoring to a vessel wall.

FIG. 1E shows another embodiment of an implantable device having a structure similar to that shown in FIG. 1C in a deployed condition outside a delivery catheter 30. In this embodiment, anchoring leg 21, terminating at corner 18, has an anchoring leg extension 28, while anchoring leg 20, terminating at corner 17, is detachably mounted to a delivery mechanism in the form of delivery wire 32. The terminal ends of each anchoring leg may be identified and distinguished by differently configured radiopaque markers, illustrated as markers 33 and 34. This embodiment thus illustrates an implantable device having anchoring leg structures with different dimensions and configurations, and also illustrates an embodiment in which one of the anchoring legs is detachably mounted to a delivery mechanism. One advantage of this embodiment is that the device may be fully deployed into position with the framework structure and closure membrane positioned across the opening of an aneurysm while the anchoring legs remain within the delivery device and/or attached to the delivery mechanism. This provides flexibility for repositioning, retracting and redeploying the implantable device prior to detachment from delivery wire 32.

The framework support structure and anchoring legs may be constructed from a variety of metallic materials, polymeric materials (e.g. polyethylenes, polypropylenes, Nylons, PTFEs, and the like), and composite materials. These components may be constructed, for example from biocompatible stainless steels, from highly elastic metallic alloys, from biocompatible shape change materials that exhibits pseudo-elastic or super-elastic behavior and/or shape memory properties, such as shape memory alloys. The shape change material changes shape in a predictable manner upon application of a shape change force such as heat, current or the like, to assume its predetermined, deployed condition. The force for producing the shape change is generally a change in temperature produced, for example, by introducing the device into a body temperature environment, by applying heat to the device using an external heating mechanism, or by heating the device by applying current through a conductive element. Upon heating of the shape memory material to, or above, a phase transition temperature of the material, the device framework structure and/or anchoring structure(s) assume their predetermined, larger dimension configuration.

Nitinol alloys exhibiting super-elastic behavior are preferred for many implantable devices described herein and may be used to construct both the framework support structure and the anchoring legs. In some embodiments. Nitinol alloys may also be used to construct a closure membrane. When metallic materials such as Nitinol are used, framework and anchoring structures may be formed, for example, from solid wire, tubular wire, braided materials, or the like, and/or may be cut (or etched or otherwise removed) from substantially flat sheets of material, or from shaped substrate materials. Framework and anchoring structures may incorporate additional materials and may have coatings or membranes provided between and among the framework structures and anchoring legs. In one embodiment, the framework and anchoring structures may be formed from a thin-film highly elastic alloy, such as a thin-film Nitinol alloy, using sputtering techniques that are known in the art. In another embodiment, described with reference to FIGS. 1A and 12A, the framework and anchoring structures may be constructed from a metallic or polymeric or composite material by cutting, or etching, or otherwise providing a preassembled shape from a substantially flat sheet substrate and subsequently shaping the preassembled shape to provide the desired deployed conformation.

The occlusive or semi-occlusive membrane is generally constructed from material(s) that are biocompatible and biostable and that are compressible, foldable or otherwise deformable for assuming a low diametric profile in a delivery condition for loading into or mounting to a delivery catheter. Suitable membranes may comprise at least one layer of flexible material and may have a substantially continuous, non-porous structure. Alternatively, occlusive or semi-occlusive membranes may have various types of porous, perforated, woven, non-woven and fibrous structures and may comprise multiple layers of material.

In one embodiment, the closure membrane is constructed from a material that is substantially impermeable to liquids such as blood and bodily fluids. Alternatively, the closure membrane may be constructed from a material that is semi-permeable or permeable to liquids, such as blood and bodily fluids, and allows at least limited fluid exchange across the membrane. Closure membrane 24 may be constructed, for example, from many types of natural or synthetic polymeric materials, polyurethanes, silicone materials, polyurethane/silicone combinations, rubber materials, woven and non-woven fabrics such as Dacron™, fluoropolymer compositions such as a polytetrafluoroethylene (PTFE) materials, expanded PTFE materials (ePTFE) such as and including TEFLON®, GORE-TEX®, SOFT-FORM®, IMPRA®, and the like.

In another embodiment, the closure membrane may comprise a metallic material, such as a thin-film shape memory alloy, e.g., a thin-film Nickel-Titanium alloy such as a Nitinol alloy or other biocompatible metals, including noble metals such as gold foils, tanalum wire and the like. The membrane may be bonded, mechanically attached or fused to the frame to provide a secure seal and device strength. In some embodiments, the membrane and structural framework component may be constructed from a single piece of material such as Nitinol, stainless steel, silicone, Dacron, ePTFE, or another polymeric material.

In some embodiments, the closure membrane comprises a mesh-like structure having a uniform or non-uniform configuration over its surface area. In general, closure membranes having a mesh configuration have a generally fine mesh structure. In some embodiments, the membrane has a mesh-like structure that is radially expandable. In other embodiments, the membrane has a mesh-like structure that is expandable along one or more axes. The closure membrane, in some embodiments, is semi-permeable and has radial flexibility sufficient to mimic the structure and movement (e.g. pulsatility) of the vessel wall or other physiological structure it's repairing. When the implantable device incorporating the framework support structure and membrane is placed across the neck of an aneurysm, for example, it may become substantially continuous with and follow the motion of the vessel wall, providing effective repair and reconstruction of the vessel wall and restoring strength, structure and flexibility to the vessel wall. In some embodiments, the framework support structure and closure membrane, and/or anchoring structures, after placement across a tissue or vessel detect, not only effectively repair the defect, but promote cellular ingrowth and re-endothelialization, thereby further incorporating the closure device in the physiological structure and reducing the opportunity for the structure to weaken and return to a structurally or functionally defective condition. The framework support structure and/or membrane may incorporate a reinforcing structure throughout its surface area, or in particular areas of its structure.

The closure membrane may be associated with a reinforcing structure throughout or at particular areas of its surface area. In one embodiment, for example, a resilient and flexible sheet material may be bonded to or associated with a more rigid reinforcing structure having a regular or irregular pattern. The membrane may have a porous or perforated surface structure over at least a portion of its surface area, with pores arranged to provide a substantially uniform porosity over the surface area, or with pores arranged to provide different porosities at different surface areas of the closure structure. The average pore size may be substantially uniform over the surface area of the closure structure, or pores having different size distributions may be provided. In general, pore sizes in the range of from about 0.5 microns to 400 microns are suitable. In one embodiment, a pore structure is provided that permits flow of liquids across the closure structure but excludes large proteins and cells, including red blood cells. In general, pores having an average diameter of less than about 10 microns will exclude large proteins and cells, while allowing fluids to penetrate and cross the membrane. The arrangement of pores may form a regular or irregular pattern and the conformation of the pores may be uniform or non-uniform and may be generally circular, elliptical, square, or the like. A higher porosity may be provided, for example, at peripheral portions of the closure structure that, following placement, are in proximity to or contacting the tissue or vessel wall.

The membrane may, alternatively or additionally, have a surface treatment provided on one or both sides that promotes cellular attachment and growth. In one embodiment, for example, the membrane material has a surface conformation that is irregular, or roughened, or incorporates surface irregularities that promote cellular attachment to the material. In another embodiment, the closure structure may have a three dimensional configuration that incorporates depressions, grooves, channels, or the like, in a regular or irregular pattern, to promote cellular attachment and re-endothelialization.

In some devices disclosed herein, the membrane and/or other structural components of the implantable device, including one or more anchoring structures, are structured or treated to promote, or comprise a material or substance(s) that promotes, cellular ingrowth or attachment at the site of deployment. Similarly, methods of the present invention may involve introduction of agent(s) that promote cellular ingrowth and re-endothelialization at the site of the device deployment prior to, during, and/or subsequently to placement of the implantable device. For vascular applications, for example, it is desirable for some applications to promote the re-endothelialization of the blood vessel at the site of an aneurysm or another vessel defect that may be repaired by placement of devices of the present invention. Numerous substances that may be used in connection with methods and systems of the present invention are described in U.S. Patent Publications 2004/087998 A1 2004/0193206 A1, which are incorporated herein by reference in their entireties.

Numerous materials may be administered prior to, during or subsequent to device deployment, or associated with the implantable device, to promote cellular ingrowth. Biocompatible materials may be used for this purpose including, for example, proteins such as collagen, fibrin, fibronectin, antibodies, cytokines, growth factors, enzymes, and the like; polysaccharides such as heparin, chondroitin; biologically originated crosslinked gelatins; hyaluronic acid; poly(.alpha.-hydroxy acids); RNA; DNA; other nucleic acids; polyesters and polyorthoesters such as polyglycolides, polylactides and polylactide-co-glycolides; polyactones including polycaprolactones; polydioxanones; polyamino acids such as polylysine; polycyanoacrylates; poly(phosphazines); poly (phosphoesters); polyesteramides; polyacetals; polyketals; polycarbonates and polyorthocarbonates including trimethylene carbonates; degradable polyethylenes; polyalkylene oxalates; polyalkylene succinates; chitin; chitosan, oxidized cellulose; polyhydroxyalkanoates including polyhydroxybutyrates, polyhydroxyvalerates and copolymers thereof; polymers and copolymers of polyethylene oxide; acrylic terminate polyethylene oxide; polyamides; polyethylenes; polyacrylonitriles; polyphosphazenes; polyanhydrides formed from dicarboxylic acid monomers including unsaturated polyanhydrides, poly(amide anhydrides), poly(amide-ester) anhydrides, aliphatic-aromatic homopolyanhydrides, aromatic polyanhydrides, poly(ester anhydrides), fatty acid based polyanhydrides, and the like; as well as other biocompatible or naturally occurring polymeric materials, copolymers and terpolymers thereof; fragments of biologically active materials; and mixtures thereof.

Some biocompatible polymers are considered to be bioabsorbable and are suitable for use in association with devices and methods of the present invention, including polylactides, polyglycolides, polylactide-co-glycolides, poly anhydrides, poly-p-dioxanones, trimethylene carbonates, polycaprolactones, polyhydroxyalkanoates, and the like. Biocompatible polymers which are not generally considered to be biodegradable may also be used, including polyacrylates; ethylene-vinyl acetates; cellulose and cellulose derivatives including cellulose acetate butyrate and cellulose acetate propionate; acyl substituted cellulose acetates and derivatives thereof; non-erodible polyolefins; polystyrenes; polyvinyl chlorides; polyvinyl fluorides; polyvinyl (imidazoles); chlorosulphonated polyolefins; polyethylene oxides; polyethylene glycols; polyvinyl pyrrolidones; polyurethanes; polysiloxanes; copolymers and terpolymers thereof; and mixtures thereof. Exemplary polymers are well known in the an and one of ordinary skill in the an would understand that such polymers are by far too numerous to list here. Thus, this list is intended for illustrative purposes only and is not intended to be exhaustive.

Non-polymeric materials may also be used on connection with membranes and implantable devices of the present invention. Suitable non-polymeric materials include, for example, hormones and antineoplastic agents. Examples of other biocompatible materials that promote integration with the vasculature of the patient include, for example, processed human or animal tissue including, for example, cells or cell fragments, engineered vascular tissue, matrix material from bladder, stomach, liver, genetic material of a natural or synthetic origin, and the like.

Other types of compositions may also be associated with a membrane, framework structure and/or anchoring structure(s) forming the implantable devices of the present invention. Hydrophilic and/or hydrophobic agents or bonding agents may be provided on all or a portion of the structure(s), for example. Similarly, friction-reducing agents, including fluoropolymers such as PTFE, may be provided on all or a portion of the structure(s) to facilitate deployment from a delivery catheter or sheath. Radiopaque markers or radiopaque compounds may be associated with certain structures or portions of device structure to facilitate accurate positioning, placement and monitoring of the deployed device. In one embodiment, for example, a radiopaque composition may be incorporated in the closure structure or provided as a coating on the closure structure. In yet another embodiment, certain therapeutic agents, antibiotic agents, thrombogenic agents, anti-thrombogenic agents, and the like may be associated with certain structures or portions of the device structure, or may be administered prior to, during or following deployment of the implantable device. Suitable agents are well known in the art and are used in connection with other types of implantable devices.

The membrane may comprise multiple layers, and may have a variety of coatings or other materials associated with it, such as adherent or bonding substances, therapeutic substances, hydrophilic or hydrophobic materials, swellable materials such as hydrogels, radiopaque markers, and the like. In one embodiment, for example, a swellable hydrogel may be provided on a surface of the closure structure and/or anchoring structures that, in a deployed condition, face or contact an internal portion of an aneurysm. In another embodiment, an agent or combination of agents that promote embolization or thrombosis may be provided on a surface of the membrane, framework support structure and/or anchoring structures that, in a deployed condition, face or contact an internal portion of an aneurysm to promote embolization inside the aneurysm. In yet another embodiment, an agent or combination of agents that reduce thrombosis and clotting, such as heparin, tissue plasminogen activator (tPA), Abciximab, and the like may be provided on a surface of the closure structure and/or anchoring structures that, in a deployed condition, face or contact a blood vessel or blood vessel wall. In still another embodiment, an agent or combination of agents that prevent restenosis and/or reduce inflammation to the site, such as Paclitaxel or a derivative or analog, Sirolimus, anti-inflammatory compositions such as steroids, statins, ibuprofen or the like, may be provided on a surface of the closure structure and/or anchoring structures. In yet another embodiment, a radioactive composition may be associated with a surface of the closure structure and/or anchoring structures for therapeutic or imaging purposes.

The membrane associated with the framework support structure placed across the neck of the aneurysm may have an opening or slot for passage of a guidewire of another delivery or targeting mechanism, or for introduction of compositions, devices, or the like subsequent to placement of the closure system. According to some methods of the present invention, additional embolic devices such as coils, liquid or particulate embolics, or the like, may be introduced through a delivery catheter inserted through an opening of the closure structure following placement of the closure structure.

The material(s) forming the membrane may be designed to incorporate various agents and/or coatings homo- or hetero-geneously provided across one or all layers to promote or retard cell growth, depending on the characteristics desired. For example, the inside surface of the covering may be coated with an agent to prevent excessive cell growth that may block the lumen of the vessel (i.e. to prevent restenosis), while the outer surface of the covering may be coated with a material designed to promote a healing response. In other embodiments, specific portions or sections of individual coverings may be coated or provided with materials having different properties.

Radiopaque markers may be incorporated into the design to position the device accurately in the vasculature. Variations in the marker geometry may be adopted to distinguish different segments of the device framework. For example, the proximal legs of the device may incorporate a marker with two dots, while the portion of the device closer to or in proximity to the covering may incorporate a single dot. Alternatively, different shaped markers may be used to differentiate different parts of the device. Radiopaque markers may be added anywhere along the device frame or attached materials, coverings, and membranes to provide spatial location of different device components and features under angiography.

Numerous specific implantable device embodiments are described below. It will be appreciated that the disclosure provided above with respect to materials and modes of construction, the structure of the framework and membrane components, the provision of radiopaque markers and other features as described above may be incorporated, as well, in the specific embodiments described below.

Figure 2F:
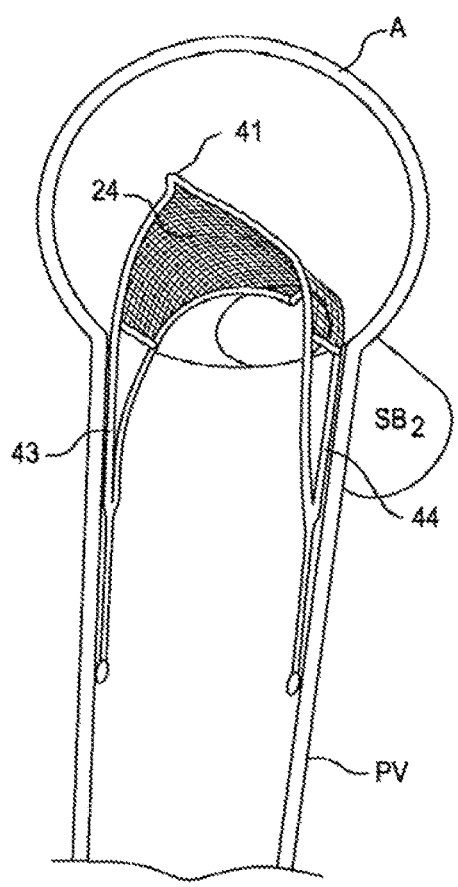

FIGS. 2A-2F show schematic drawings illustrating the transition of an implantable device of the present invention from a small diameter, folded delivery condition inside a distal end of a delivery catheter (FIG. 2A) to a larger diameter, deployed condition implantable device having the framework support structure positioned across the neck of an aneurysm and the anchoring legs positioned contacting the walls of a neighboring blood vessel, such as the parent vessel (FIGS. 2E, 2F). Framework structures, closure membranes and anchoring legs are foldable and deformable for delivery using a small diameter catheter, yet provide structural integrity, durability and a substantial degree of rigidity in a larger diameter, deployed condition.

In one embodiment, the framework structure, the closure membrane and the anchoring structures are generally radially compressed along the delivery axis and arranged in a substantially cylindrical, delivery configuration in a delivery catheter. In another embodiment, the implantable device may be stored in a protective container in an expanded, deployed condition, with the delivery mechanism (e.g. delivery wire or tube) packaged in hoops, as is known in the art. A loading sheath may be provided, into which the implantable device is loaded to assume a smaller diameter delivery condition prior to being transferred to a delivery catheter for navigation to the target deployment site.

In embodiments that utilize a pusher system, the pusher is associated with a proximal end of one or both of the anchoring devices and can translate the closure device in relationship to the delivery catheter. Deployment may be achieved by a combination of actively pushing the device out of a delivery catheter and actively withdrawing the delivery catheter while maintaining the device in a stationary condition. In an alternative embodiment, implantable devices incorporate a detachment element that is released or detached following deployment. Detachment mechanisms known in the art, including mechanical, electrolytic, hydraulic, thermal and other systems, may be utilized for deployment of the implantable devices disclosed herein.

FIG. 2A shows framework structure 40 and anchoring legs in a small diameter, delivery condition mounted near the distal end of delivery catheter 45. The lateral corners 41, 42 of the framework structure 40 are positioned distally in the delivery condition. In one embodiment, a proximal end of each of the anchoring legs is detachably mounted to an independent delivery wire. Independent delivery wires may be joined proximally of their detachable mounting to anchoring legs at a common delivery wire 49 that extends proximally for the length of the delivery catheter.

FIG. 2B shows a distal end of delivery catheter 45 positioned in proximity to the neck of aneurysm A formed at an end of a neighboring vessel, such as parent vessel (PV) where two side branch vessels $SB_1$ and $SB_2$ diverge. The delivery wires and delivery catheter 45 have been moved with respect to one another to initiate the deployment of the framework structure 40. In the initial stages of deployment, the lateral corners 41, 42 aligned on the longitudinal centerline CL of the framework support structure project from the distal end of delivery catheter 45 and expand laterally toward their deployed configuration. The membrane structure 24, if one is employed, is deployed and positioned across the neck of the aneurysm as the lateral corners expand to their fully deployed position. Deployment of this device, including both the framework support structure and anchoring legs, is generally smooth and consistent as the tapered framework legs and anchoring legs are easily and smoothly pushed from the distal end of a sheath or delivery catheter.

As the deployment proceeds, as shown schematically in FIGS. 2C and 2D, the delivery catheter is moved proximally along parent vessel PV and lateral corners 41, 42 of the framework support structure expand to their fully deployed configuration. The implantable device is positioned, as shown in FIG. 2D, with at least lateral corners 41, 42 aligned on the longitudinal centerline CL positioned to contact the tissue in proximity to the neck of the aneurysm. Anchoring legs 43, 44 are deployed generally opposite one another along surface areas of the parent vessel to support and retain the implantable device in place.

In the deployed condition, as illustrated in FIGS. 2E and 2F, the distal portion of the inverted U-shaped framework support structure is positioned across the neck of the aneurysm, with lateral corners 41, 42 of the framework support structure positioned in proximity to, and generally contacting, tissue in proximity to the neck of the aneurysm. Depending on the size and configuration of the implantable device and the size, position and character of the aneurysm, the aneurysm neck and the adjoining vessel wall, the lateral corners of the framework structure may extend to contact more or less tissue of the aneurysm neck and adjoining vessel wall. In some embodiments, the perimeter of the framework structure may be larger, in all areas, than the neck of the aneurysm and the entire perimeter of the framework structure may contact the neck of the aneurysm or vessel wall following deployment. In other embodiments, the framework corners or associated wingtip extensions aligned on the longitudinal centerline CL and regions of the perimeter structure in proximity to the framework corners contact tissue at or near the aneurysm neck following placement and deployment, while other portions of the framework perimeter are unsupported by, or positioned internally of the neck of the aneurysm following deployment.

In the embodiments illustrated in FIGS. 2E and 2F, the inverted substantially U-shaped perimeter support structure and associated closure membrane 24 substantially cover the neck of the aneurysm and extend circumferentially to contact tissue surrounding both sides of the neck of the aneurysm, or the vessel wall adjacent the neck of the aneurysm, at locations between the lateral corners and proximal to the longitudinal centerline CL of the device. In the embodiments schematically illustrated in FIGS. 2E and 2F, for example, areas of the perimeter support structure and closure membrane 24 proximal to the longitudinal centerline CL and distal to anchoring legs 43, 44 generally contact and support tissue, including the vessel wall, located circumferentially of and in proximity to the neck of the aneurysm. Anchoring legs 42, 44, including proximal extensions, contact the wall of a neighboring vessel, such as parent vessel PV, to anchor and support the curved framework support across the neck of the aneurysm.

Figure 3A:
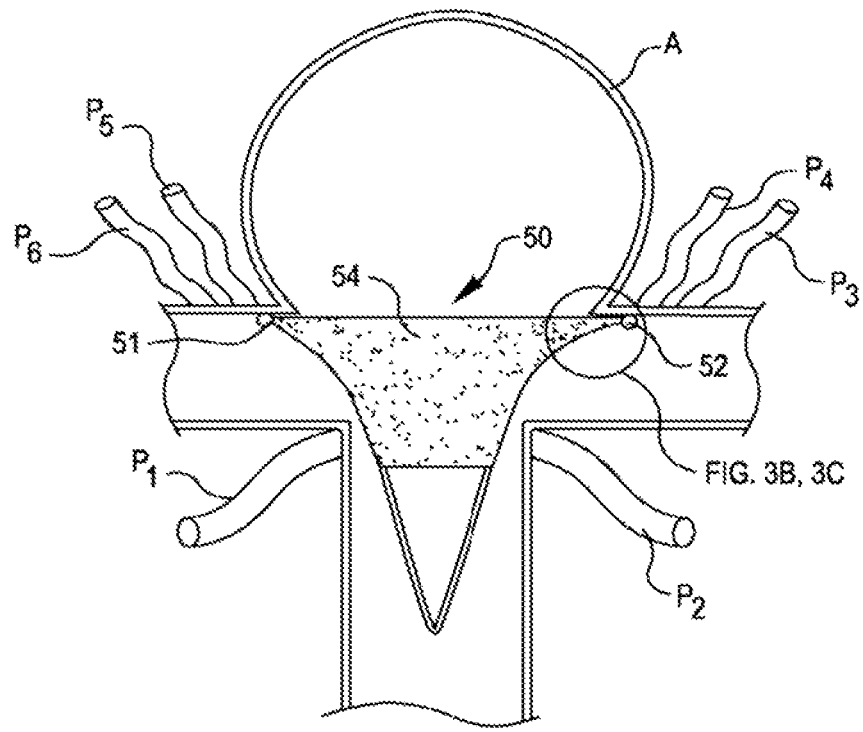
FIG. 3A shows a schematic side, cut-away view of another embodiment of an implantable device of the present invention deployed across the neck of a terminal aneurysm.
Figure 3B:
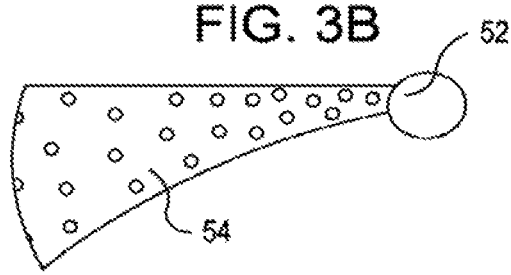
FIGS. 3B and 3C show an enlarged plan view of alternative configurations of a portion of the device as indicated in FIG. 3A.

As shown schematically in FIGS. 3A and 3B, perforating vessels and sidebranches (shown schematically as $P_1$-$P_6$)

often develop near aneurysm locations. An implantable device 50 having a porous covering 54 may be advantageously deployed in this circumstance to preserve flow in the perforating vessels and side branches. In some applications, it may be advantageous to vary the porosity across the surface area of the covering. An area that primarily covers the neck of the aneurysm A, for example, may nave lower porosity (e.g., fewer pores, lower pore density, smaller pores, etc.) than an area that overlaps the neck of the aneurysm and contacts a vessel wall ($SB_1$, $SB_2$) in the area of the aneurysm neck. This may be accomplished, for example, by varying the pore size and/or spacing of the pores, to promote maintenance of patency of perforating vessels $P_1$-$P_6$ near the aneurysm neck. FIG. 3B illustrates a section of porous covering 54, wherein the pore density in the region near lateral corner 52, where the framework support perimeter structure contacts the aneurysm neck or vessel wall, has a higher pore density than mom centrally located portions of closure membrane 54.

Figure 3C:
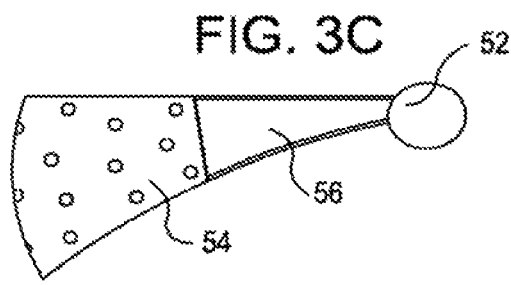

In alternative embodiments, very large pores or openings may be provided in areas where the framework support perimeter structure contacts the aneurysm neck or vessel wall. In the embodiment schematically illustrated in FIG. 3C, for example, closure membrane 54 does not extend to lateral corner 52 of the framework support perimeter structure, but terminates a distance from corner 52, leaving an opening 56 in the framework support perimeter structure that facilitates flow and reduces occlusion of perforating vessels. In this embodiment, the closure membrane may be sized and configured to extend to the edges, or just past the edges, of the aneurysm neck, while the lateral corners, or wingtip extensions of framework support structure may be sized and configured to extend further, providing support and contact along the vessel wall for a distance away from and in proximity to the neck of the aneurysm.

Figure 4A:
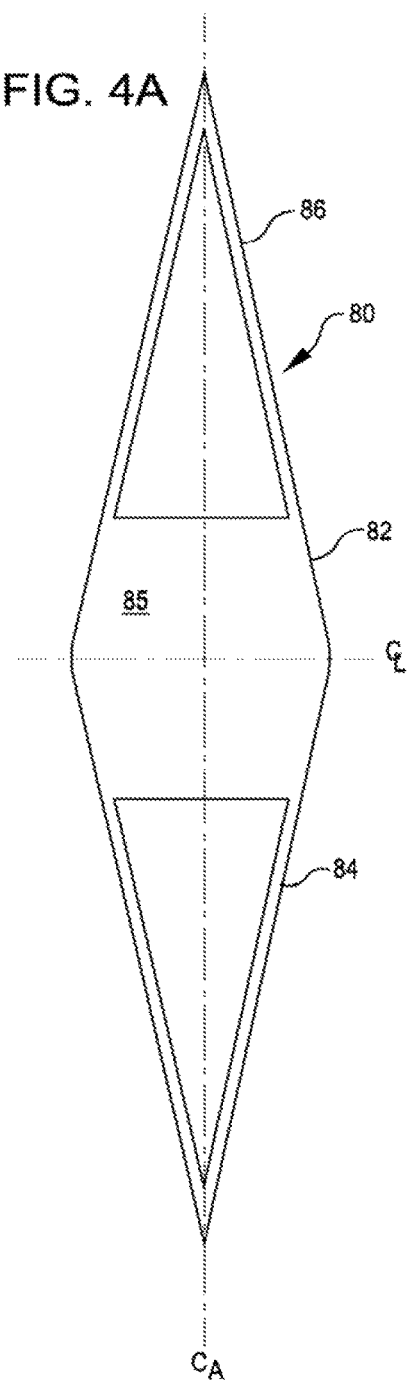
FIG. 4A shows a schematic plan view of another embodiment of an implantable device of the present invention in a substantially flat, unassembled configuration.
Figure 4B:
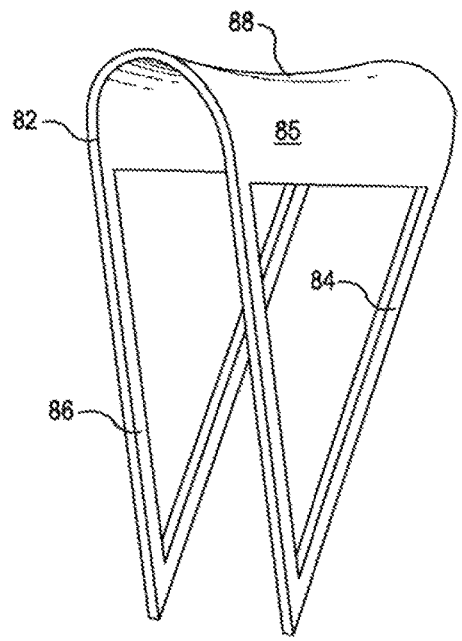
FIG. 4B shows a schematic side perspective view of the implantable device of FIG. 4A in a folded, assembled configuration.
Figure 4C:
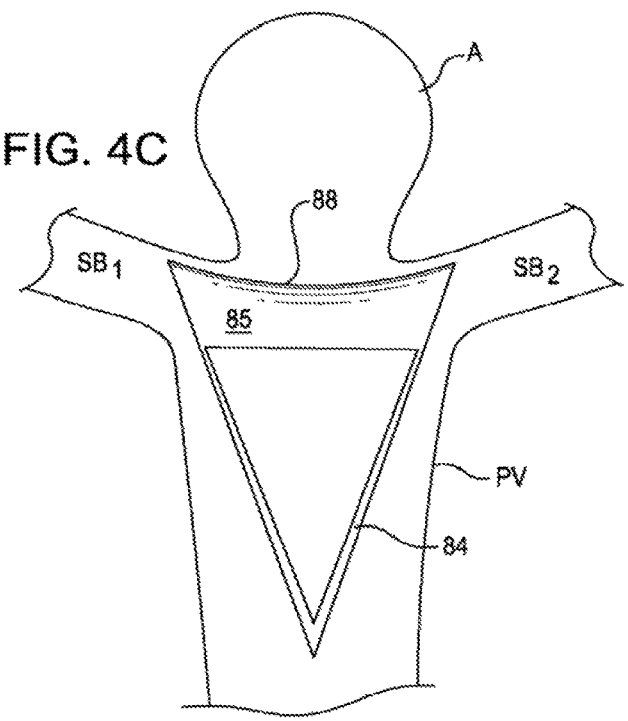
FIG. 4C shows a schematic side, cut-away view of the implantable device of FIG. 4B deployed across the neck of a bifurcation aneurysm.

FIGS. 4A-4C schematically illustrate another embodiment of an implantable device 80 of the present invention. FIG. 4A shows implantable device 80 in a substantially flat, pre-assembled configuration, while FIG. 4B schematically shows the device of FIG. 4A. In a three-dimensional, inverted U-shaped deployed condition, and FIG. 4C schematically shows the device of 4B in a deployed condition across the neck of an aneurysm A. Implantable device 80 comprises a framework support structure 82 having a generally diamond-shaped configuration in a pre-assembled, flat condition, as shown in FIG. 4A. In this embodiment, the framework sides join in the region of longitudinal centerline CL at a widest portion of the framework perimeter support structure and taper to form anchoring legs 84, 86. A closure membrane 85 is formed integrally with or mourned to the framework support structure and extends for a distance on both sides of longitudinal centerline CL.

Implantable device 80 may be constructed from the pre-assembled form of FIG. 4A to the assembled form illustrated in FIG. 4B simply by folding the device along longitudinal centerline CL and bringing the terminal ends of anchoring legs 84, 86 toward one another to provide the substantially inverted U-shaped configuration illustrated in FIG. 4B. In the assembled configuration, the framework support structure and closure membrane 85 form a curved, inverted U-shaped structure, while anchoring legs 84, 86 extend proximally from the curved framework support structure along substantially parallel planes spaced a distance from one another.

The framework support structure and closure membrane of implantable device 80 additionally present a shaped, curved leading surface 88 configured to engage the anatomical structure of the neck of aneurysm A, and to provide a more precise fit of the leading surface across the neck and opening of the aneurysm. Leading surface 88 has a generally concave curved, saddle-shaped configuration along the longitudinal centerline CL with the elevated portions of the curved structure positioned generally in proximity to the framework perimeter structure. While the curved configuration is illustrated as being generally symmetrical with respect to the axial centerline CA of the implantable device, it will be appreciated that non-symmetrical curves may be desirable for particular applications. In some embodiments, the curved leading surface may take the form of a convex curve, while in other embodiments, complex curves, such as curves having hyperbolic paroboloid structures, may be used and may involve extend over larger regions of the framework structure and/or closure membrane. Implantable devices having this curved configuration may be effective and stable even with reduced contact of the framework support structure with vessel walls in proximity to the neck of the aneurysm. In embodiments in which shaped leading surface 88 is substantially impermeable to fluids, leading surface 88 may provide effective diversion of blood flow from the aneurysm neck and reduce obstruction of the sidebranch vessels $SB_1$ and $SB_2$.

Figure 5A:
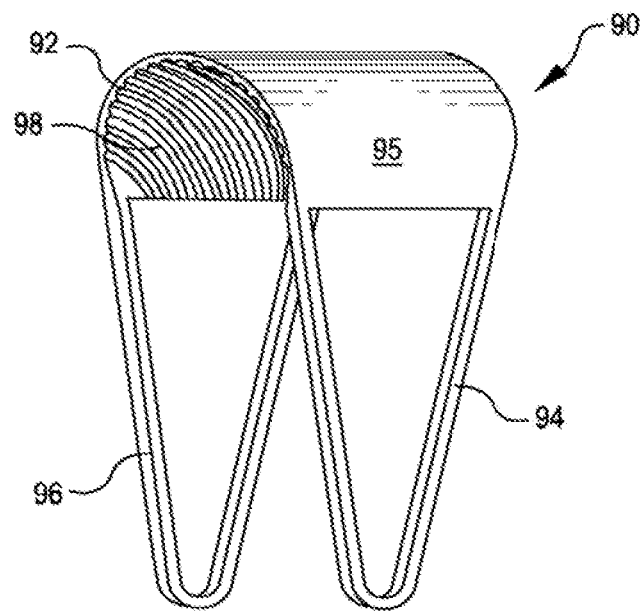
FIG. 5A snows a schematic side perspective view of another embodiment of an implantable device of the present invention incorporating a contoured flow diversion membrane.
Figure 5B:
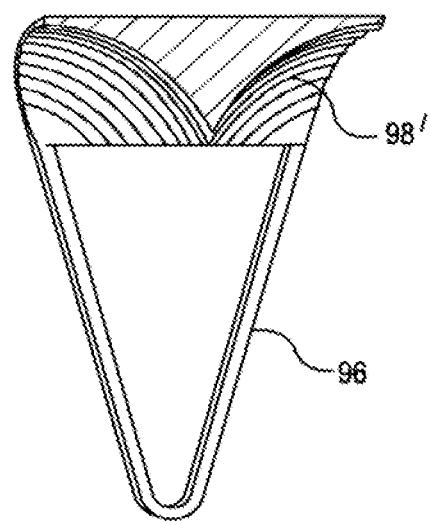
FIG. 5B shows a schematic side perspective view of another embodiment of an implantable device of the present invention incorporating a contoured flow diversion membrane.

FIGS. 5A and 5B schematically show additional embodiments of an implantable device of the present invention. FIGS. 5A and 5B illustrate implantable devices 90 comprising a framework support structure 92 having a generally inverted U-shaped configuration and two anchoring legs 94, 96 extending from the curved framework support structure along substantially parallel planes spaced a distance from one another and terminating in curved distal ends.

The curved framework support structure may be substantially continuous or may be associated with a substantially continuous membrane 95 having microfeatures or microtextures or contours 96 provided along the surface facing (proximally) toward the anchoring legs 94, 96. Contoured surface 96 is exposed to blood flow following deployment of the device and functions to direct blood flow away from the neck of the aneurysm and/or down a sidebranch vessel. Microfeatures, micro-textures or contours 96 may be formed in a fluid impermeable substrate material using a variety of techniques and may assume a variety of configurations. A simple curved, grooved configuration is illustrated in FIG. 5A, while a more complex grooved structure is illustrated in FIG. 5B. Implantable devices having these features may be sized and configured, as described above, to substantially cover the neck of the aneurysm, with the curved framework structure contacting the vessel wall in proximity to the aneurysm neck. Alternatively, implantable devices incorporating microfeatures, microtextures or contours for directing and diverting blood flow may be sized and configured to partially cover the neck of the aneurysm and may effectively redirect blood flow away from the aneurysm without fully occluding the neck of the aneurysm.

Figure 6A:
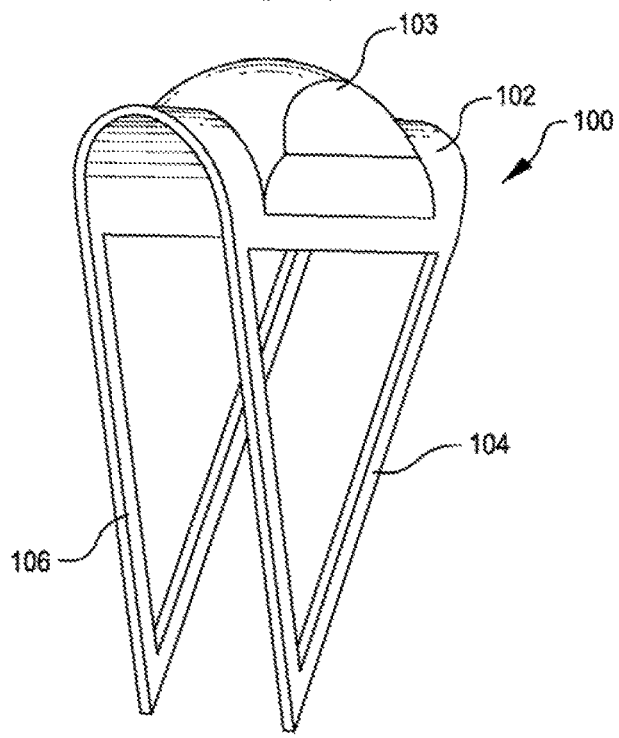
FIG. 6A shows a schematic side perspective view of another embodiment of an implantable device of the present invention.
Figure 6B:
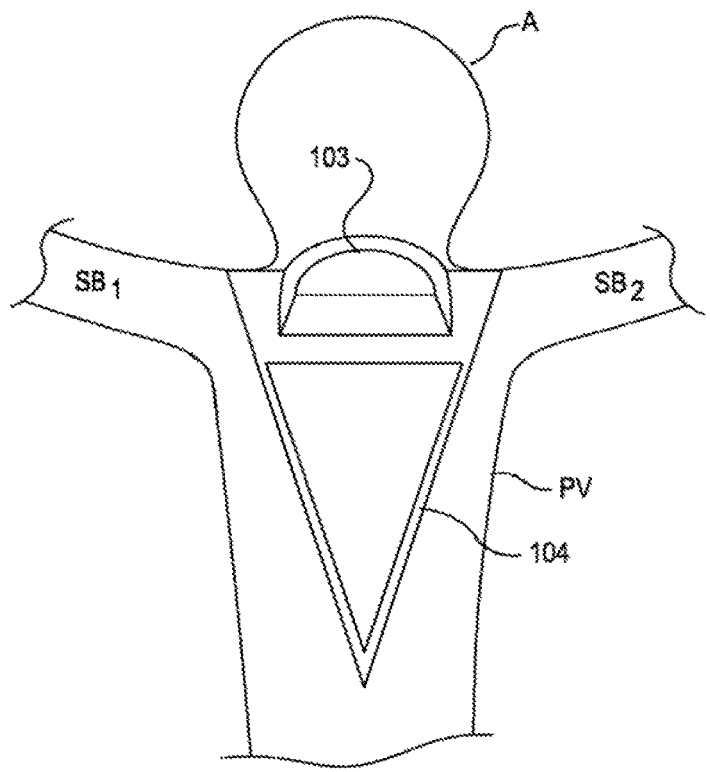
FIG. 6B shows a schematic side, cut-away view of the implantable device of FIG. 6A deployed across the neck of a bifurcation aneurysm.

FIG. 6A schematically shows another embodiment of an implantable device 100 of the present invention, and FIG. 6B schematically shows the device of FIG. 6A deployed across the neck of an aneurysm A. Implantable device 100 comprises a framework support structure 102 having a generally inverted U-shaped configuration and two anchoring legs 104, 106 extending from the curved framework support structure along substantially parallel planes spaced a distance from one another. Implantable device 100 additionally comprises a shaped, curved leading surface 103 projecting out of the plane of the framework support structure and configured to engage the anatomical structure of the neck of aneurysm A. Implantable devices having a shaped, curved leading surface may be desirable in certain circumstances to provide a more precise "fit" of the leading surface across the neck and opening of the aneurysm, and to engage the aneurysm distally as well as radially. The contour of leading surface 103 is designed to better seat and accommodate the neck inner surface at self-centering points of apposition.

Figure 6C:
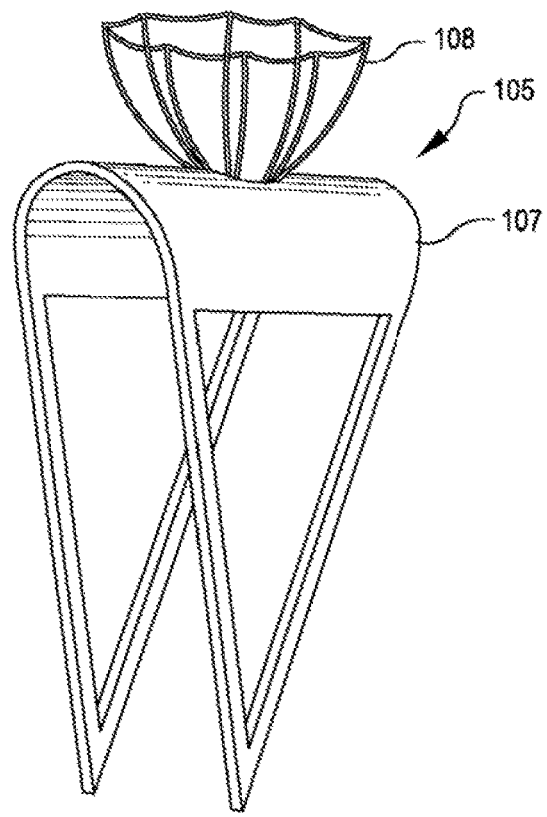
FIG. 6C shows a schematic side perspective view of another embodiment of an implantable device of the present invention.
Figure 6D:
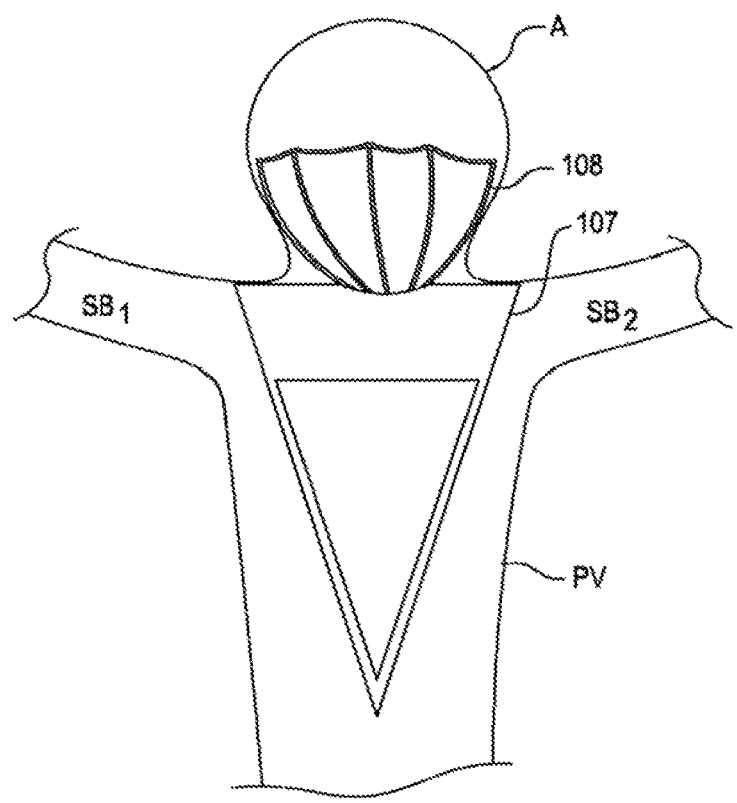
FIG. 6D shows a schematic, side, cut-away view of the implantable device of FIG. 6C deployed across the neck of a bifurcation aneurysm.

FIG. 6C snows yet another embodiment of an implantable device 105 of the present invention, and FIG. 6D schematically shows the device of FIG. 6C deployed across the neck of an aneurysm A. Implantable device 105 comprises a framework support structure 107 having a generally inverted U-shaped configuration and two anchoring legs extending from the curved framework support structure along substantially parallel planes spaced a distance from one another. Implantable device 105 additionally comprises an additional structure 108 that projects from a leading surface of the framework support structure or closure membrane in a direction opposite of the extension of the anchoring legs. The additional structure may be sixed and configured, as shown, for placement within an aneurysm or cavity in a deployed condition. In the embodiment illustrated in FIG. 6D, the additional structure is generally conformable to the interior surface of an aneurysm and may, upon deployment, form a basket-like shape. The structure may serve to retain debris or embolic materials inside an aneurysm cavity following placement, and may additionally serve to reinforce the aneurysm wall. The surface of the structure may additionally be covered and, following deployment, may serve to redirect flow away from art aneurysm. While a basket-like structure is illustrated, it will be appreciated that many different types of reinforcing structures may be provided.

FIGS. 7A and 7B illustrate yet additional embodiments of implantable devices 110, 110' of the present invention comprising a generally inverted U-shaped framework support structure 112, 112' having a configuration similar to that shown in FIGS. 1B-1E and having an occlusive or semi-occlusive membrane 114, 114" associated with the substantially inverted U-shaped framework structure. Anchoring legs 116, 118 extend (proximally) away from the framework support structure and closure membrane 114, aligned on substantially parallel planes. In this embodiment, anchoring legs 116, 118 and 116', 118' are formed using a combination of multiple geometrical structures, such diamonds 120, 120', triangular structures 124, 124' and curved segments 122. Curved segments 122 illustrated in FIG. 7A may be generally sinusoidal and provide flexure or bending of the anchoring legs and framework support structure laterally, facilitating positioning of the framework support structure and closure membrane across the neck of an aneurysm having an angled entrance. Curved segments may comprise substantially S-shaped (or backwards S-shaped) segments, as shown, and they may comprise other sinusoidal profiles.

Alternatively, in the embodiment shown in FIG. 7B, anchoring legs 116', 118' incorporate one or more articulating joints 125 to provide flexure and rotation of the framework support structure and closure membrane. Articulating joints 125 may provide limited angular articulation of the framework support structure and proximal portions of the anchoring legs in a single direction, or in both directions from a neutral position. A ball and socket joint may be used, for example, to provide multi-directional flexing of the framework support structure and closure membrane.

FIGS. 7A and 7B also illustrate radiopaque markers 113, 115 and 113', 115' provided in proximity to the lateral corners of framework support structure 112 and distinctive radiopaque markers 121, 123 and 121', 123' provided in proximity to the terminal (proximal) ends of anchoring legs 116, 118, and 116', 118'. It will be appreciated that additional radiopaque markers may be provided or that radiopaque materials may be incorporated in the materials comprising the structure of the implantable device, including a closure membrane, to provide additional visibility during positioning and deployment.

Figure 8:
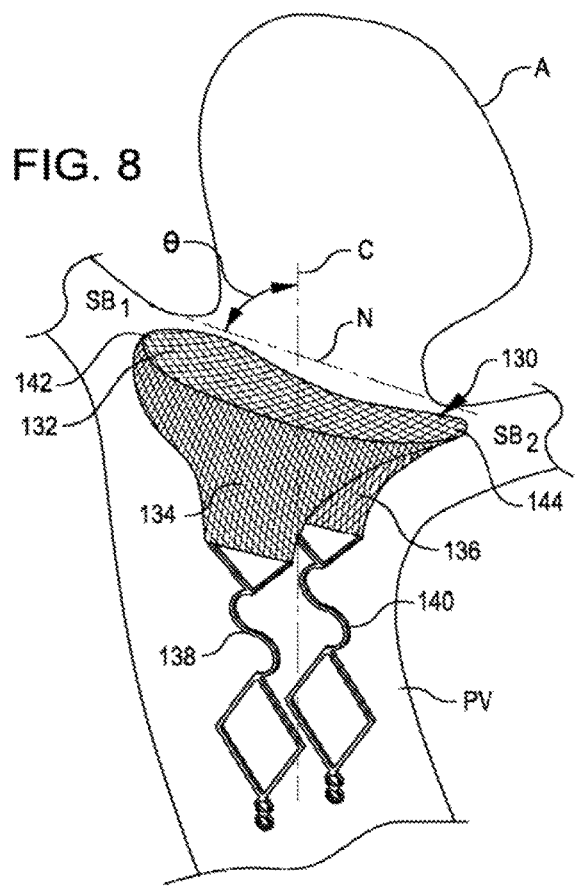
FIG. 8 shows a schematic side perspective view of another embodiment of an implantable device of the present invention having an alternative framework structure and cover configuration deployed across the neck of a bifurcation aneurysm.

FIG. 8 schematically illustrates yet another embodiment of an implantable device of the present invention in a deployed condition at the neck of an aneurysm A. In the embodiment illustrated in FIG. 8, device 130 has a configuration that accommodates and is conformable to angulation of the aneurysm neck region. The neck region angulation may be quantified as an angle .theta. formed by a line N drawn on one axis across the neck of the aneurysm relative to the centerline C of the parent vessel PV of the vessel bifurcation. It will be appreciated that angle .theta. may change when viewed from different axes crossing the neck of the aneurysm. In this embodiment, the device support structure and coveting membrane form multiple discrete surfaces that, in combination, form a generally angulated inverted U-shaped profile.

In the embodiment shown in FIG. 8, implantable device 130 incorporates an elongated, generally oblong interface surface 132 defined, in part, by a perimeter structure and two adjoining side surfaces 134, 136 extending proximally from interlace surface 132 generally opposite one another. Interface surface 132 has at least one dimension larger than the neck of the aneurysm and provides lateral edges 142, 144 for contacting the neck of the aneurysm when deployed, or for contacting the vessel wall in proximity to the neck of the aneurysm. Side surfaces 134, 136 may be substantially flat, as shown, or may be curved, and generally contact the vessel wad adjacent to the aneurysm neck and between side branch vessels. Anchoring legs 138, 140 extend from proximal regions of side surfaces 134, 136 and, when deployed, contact the side walls of parent vessel PV. The anchoring legs may incorporate a flexure mechanism to facilitate positioning and placement of the device during deployment, as shown.

Implantable devices of this type may incorporate multiple angulated covering surfaces aligned on different planes, or curved surfaces, to provide enhanced coverage of an opening and conformity to vessel walls in proximity to the opening. Interface surface 132 may be curved substantially along the longitudinal centerline, or along another axis to facilitate the fit over the opening. Interface surface 132 of the device shown in FIG. 8, is illustrated forming a curved depression, for example. Other types of carved configurations, including convex and concave curved configurations, as well as more complex curved configurations, such as hyperbolic paraboloid curved configurations, may also be used. Generally matching, symmetrical "side" surfaces 134, 136, illustrated having a mesh-like configuration, may be provided having differently oriented surfaces to provide enhanced contact with vessel walls in proximity to the opening. In addition, interface surface 132 and side surfaces 134, 136 may not be symmetrical with respect to an axial centerline C of the device, with a greater interface and side surface area provided on one side of the axial centerline than the other. As shown in FIG. 8, for example, lateral edge 142 of interface surface 132 may be beneficially oriented distally with respect to the opposite lateral edge 144 following deployment.

Figure 9:
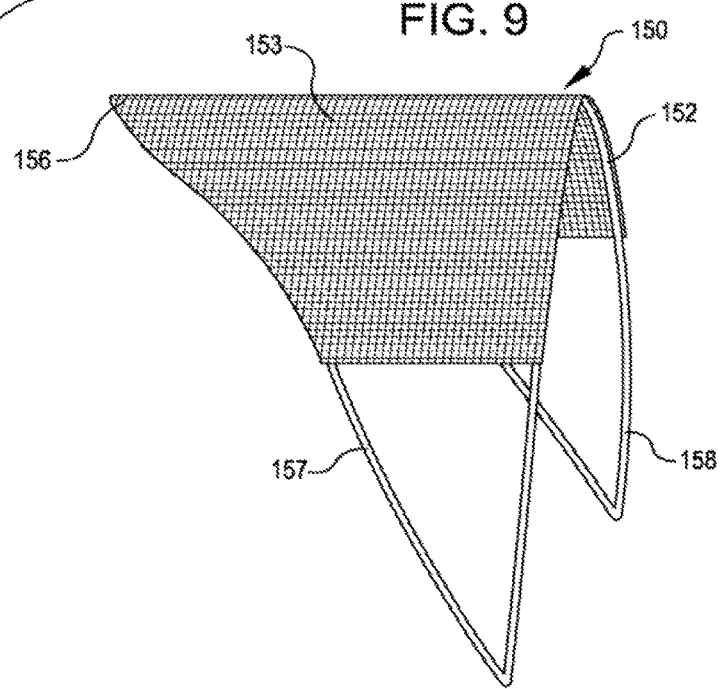
FIG. 9 shows a schematic side perspective view of another embodiment of an implantable device of the present invention having an asymmetrical framework structure and cover configuration.

FIG. 9 illustrates yet another embodiment of an implantable device of the present invention. As shown in FIG. 9, implantable device 150 may have an asymmetrical, generally inverted U-shaped framework support 152 having, for example, a generally flat edge 154 and a tapered extending edge 156. Implantable device 150 also incorporates a membrane 153 and two anchoring legs 157, 158 extending proximally from the framework support and membrane when deployed and aligned on substantially parallel, spaced apart planes. While this simple asymmetrical configuration is shown and described, it will be appreciated that many other asymmetrical configurations may be employed . . . .

Figure 10A:
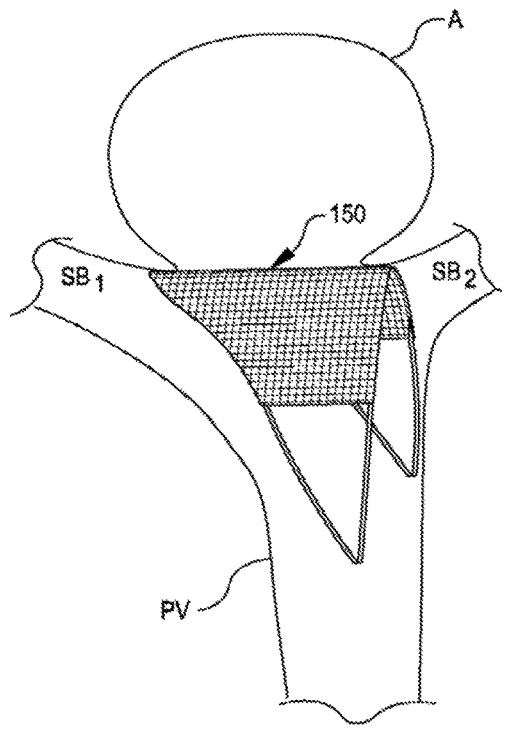
FIGS. 10A-10C show schematic side perspective views of the implantable device of FIG. 9 deployed across the neck of an aneurysm in different configurations.
Figure 10B:
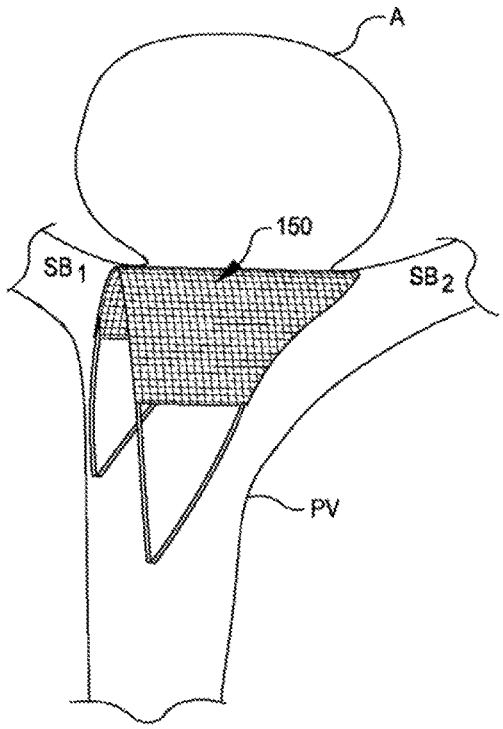
Figure 10C:
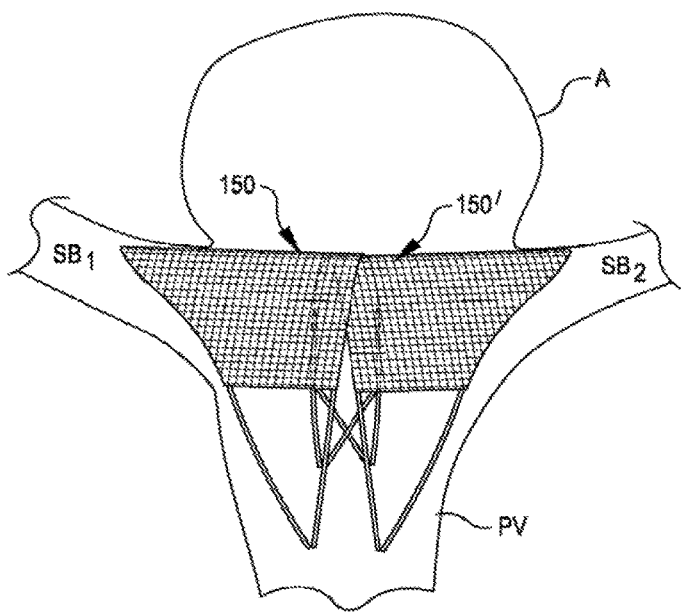

The device of FIG. 9 is shown schematically deployed in FIGS. 10A and 10B across the necks of aneurysms that are offset with respect to the parent vessel. Multiple asymmetrical devices of the type shown in FIG. 9 may also be used in combination across the neck of an aneurysm, such as a wide neck aneurysm, as illustrated schematically in FIG. 10C. A first implantable device 150 covers a distance over the neck of the aneurysm, and a second implantable device 150' is deployed complete cover the neck of the aneurysm. This results in a nominal overlap of the devices 150, 150' in a central area and provides full coverage across the aneurysm neck. One advantage of the implantable device configuration shown in FIG. 9, as evidenced by the deployment strategies illustrated in FIGS. 10A-C, is that the device may be used in different orientations, e.g. by rotating the device 180.degree., to satisfy different coverage requirements and may be used in combination to satisfy other coverage requirements.

Figure 11:
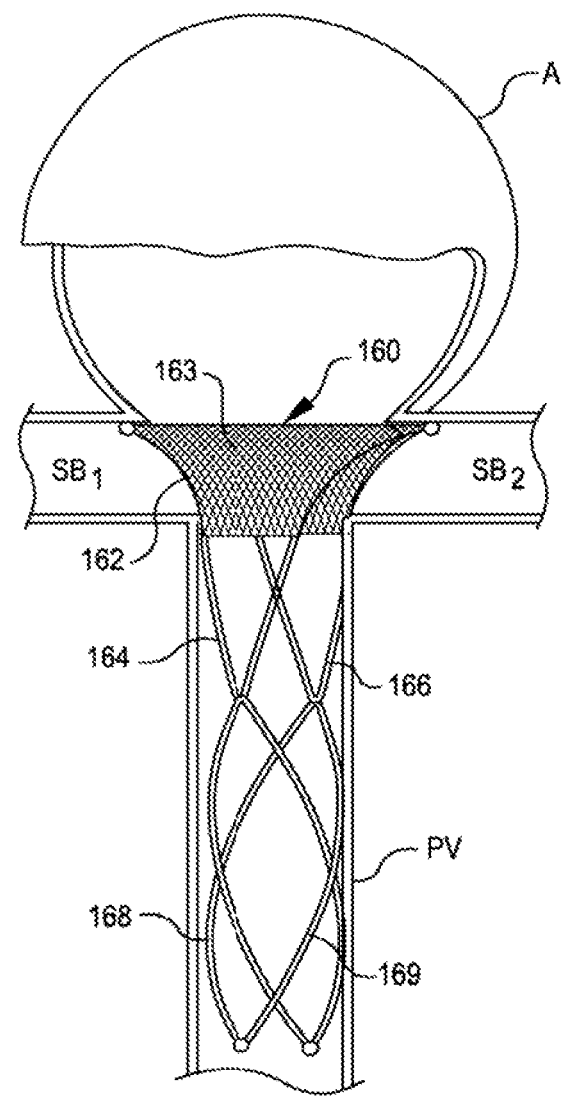
FIG. 11 shows a schematic side perspective cut-away view of another embodiment of an implantable device of the present invention deployed across the neck of a terminal aneurysm.

A device embodiment similar to the device illustrated in FIG. 1 incorporating anchoring legs having a different configuration is illustrated in a deployed position across an aneurysm opening in FIG. 11. As shown in FIG. 11, an implantable device 160 having a generally inverted U-shaped framework support structure 162 and an occlusive or semi-occlusive membrane 163 associated with the support structure may be deployed across an aneurysm neck to block or redirect blood flow into the aneurysm A. In this embodiment, implantable device 160 incorporates two generally triangular anchoring legs 164, 166 that extend proximally from the framework support structure on substantially aligned, spaced apart planes and contact the wall of parent vessel PV along generally opposite surface areas.

When implantable device 160 is deployed, as illustrated in FIG. 11, anchoring segments 164, 166 contact the parent vessel PV wall along a substantial portion of their length to maintain the framework support structure 162 and membrane 163 in place across the neck of the aneurysm. Proximal anchoring segments 168, 169 are contoured in a deployed position and extend out of the plane of distal anchoring segments 164, 166, crossing the parent vessel PV to contact the vessel in an area substantially opposite and distal from the region where anchoring segments 164, 166 contact the parent vessel PV wall. The contour of proximal anchoring segments 168, 169 may facilitate biasing distal anchoring segments 165, 167 against the vessel wall. Additionally, configuration of the multiple anchoring segments may facilitate smooth retraction of the device into the delivery system so that repositioning may be achieved if needed.

Figure 12A:
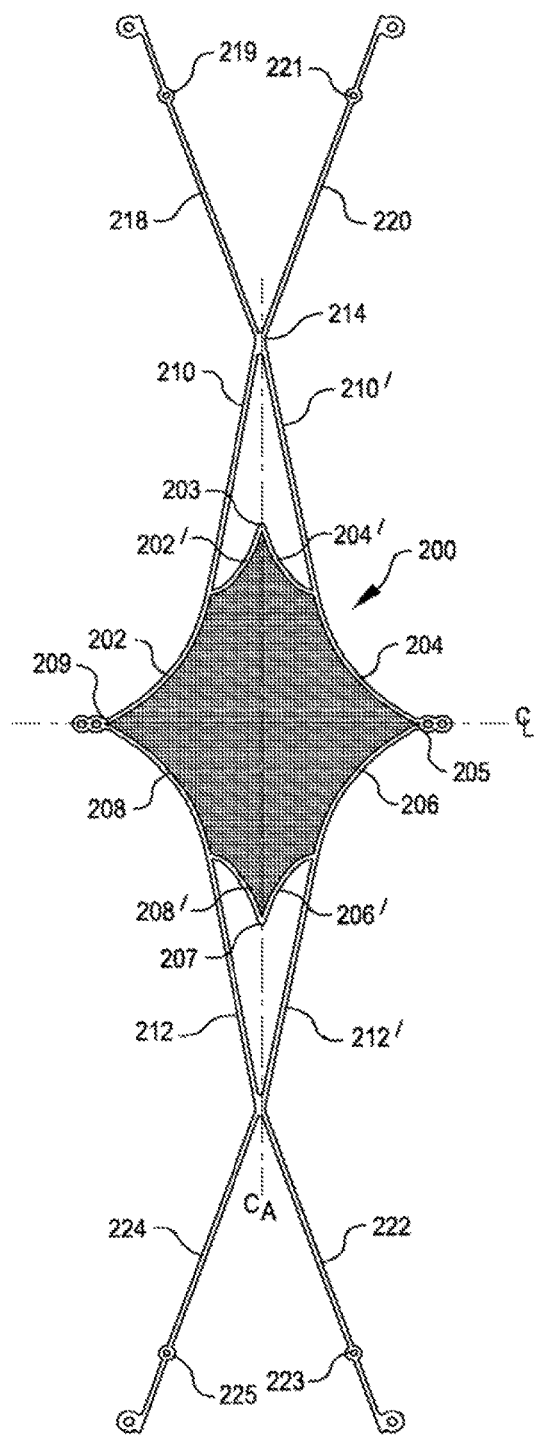
FIGS. 12A-12D snow schematic views of yet another embodiment of an implantable device of the present invention.
Figure 12B:
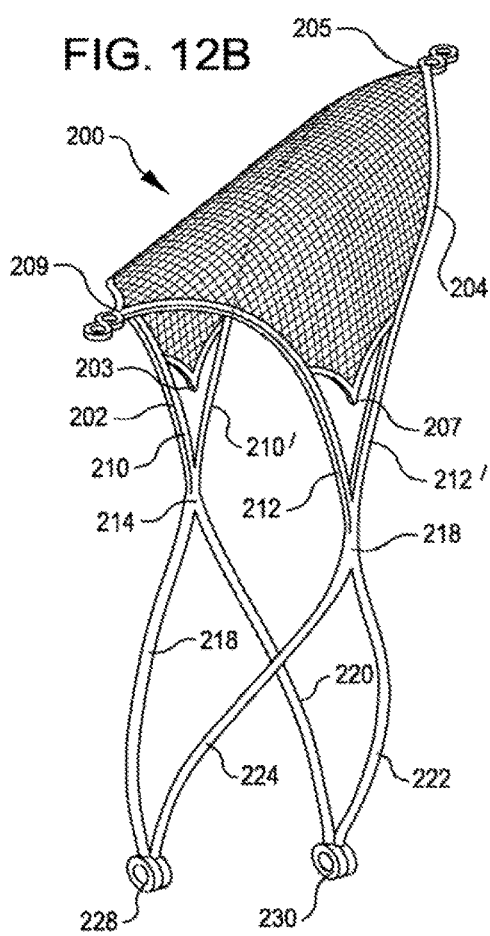

FIGS. 12A-12D illustrate yet another embodiment of an implantable device of the present invention. FIGS. 12A and 12B schematically illustrate an implantable device 200 of the present invention in a substantially flat, pre-assembled configuration (FIG. 12A) and in a folded, assembled, deployed configuration (FIG. 12B). As shown in FIG. 12A, in a substantially flat, preassembled configuration, implantable device 200 comprises a framework support structure having a modified diamond-shaped configuration formed by framework sides 202, 204, 206, 208 meeting at corners 203, 205, 207 and 209. Each of the framework sides 202, 204, 206, 208 has a complex, curved, tapered configuration with a first segment carving inwardly from a lateral corner (205, 209) aligned on lateral centerline CL and joining a second segment 202, 204', 206', 208' that curves inwardly to meet an adjacent segment at an axial corner (203, 207) aligned on axial centerline CA. Framework sides 202, 204 and 206, 208 are arranged in a mirror-image configuration. While corners 203, 205, 207, 209 are illustrated as being angular, it will be appreciated that the corners may have a curved profile, or a yet more complex configuration. The framework sides 202, 204, 206 and 208 may likewise take a variety of curved or angular configurations and may be formed integrally with one another, or separately, with separate framework sides being bonded to one another at the corners.

In the embodiment shown in FIG. 12A, anchoring segments 210, 210' and 212, 212' are formed integrally with the framework support structure and extend from framework side segments to form anchoring legs having a generally planar triangular structures. Anchoring legs 210, 212 each terminate in a junction 214, 216, respectively. In this embodiment, anchoring leg extensions 218, 220, 222, 224 extend angularly from junctions 214, 216 and have bonding points 219, 221, 223, 225 near their terminal ends. Extensions of terminal ends 219, 221, 223, 225 may be provided, as illustrated in FIG. 12A, for convenient handling of the preformed assembly and are generally removed during assembly. The implantable device shown in FIGS. 12A and 12B, including the framework structure and the anchoring legs, may be constructed from a substantially flat substrate by cutting, etching (or otherwise) the framework shape from a substrate sheet.

Implantable device 200 may be formed from the pre-assembled form of FIG. 12A to the assembled form shown in FIG. 12B by folding the pre-assembled form along longitudinal centerline CL and bringing corners 203 and 207 toward one another, forming a substantially inverted U-shaped framework support structure with the corners 205, 209 arranged on the longitudinal centerline CL positioned substantially at the midline of the curved portion of the inverted U-shaped structure and corners 203, 207 forming the proximal ends of the inverted U-shaped framework support structure. The curved framework support structure is designed and configured to contact and support tissue in proximity to an opening or cavity such as an aneurysm. Anchoring legs formed by anchoring segments 210, 210' and 212, 212' extend proximally (when positioned at a target site) from the curved framework support, forming the legs of the inverted U-shaped structure. In the embodiment illustrated in FIG. 12B, the anchoring legs formed by anchoring segments 210, 210' and 212, 212' form generally triangular structures arranged in planes that are substantially parallel to one another and spaced a distance from one another. These anchoring legs 210, 212 are designed to contact and be supported by parent vessel walls in proximity to (and generally across from) the aneurysm when the curved framework support is placed across the neck of the aneurysm.

Implantable device 200 illustrated in FIGS. 12A and 12B additionally incorporates proximal anchoring leg segments formed by joining opposing leg extensions 218, 224 and 220, 222 at proximal junctions 228, 230. The proximal anchoring leg segments may be formed by simply joining respective sets of terminal ends 219, 225 and 221, 223 to one another using welding, bonding or other stable fastening mechanisms. It may be desirable, in some applications, to reduce the rigidity and surface dimensions of the proximal junctions. FIGS. 15A and 15B illustrate one solution for joining leg extensions using cooperating/interlocking structures that reduce the thickness of the junction. FIGS. 15A and 15B snow a one leg extension terminating in a ball 227, and the other leg extension terminating in a mating socket 229. Other types of mechanically mating, or locking joints may also be provided, and suitable mechanisms for bonding mechanically mating leg extensions, such as bonding, welding, and the like, are well known. In one embodiment, the cooperating structures used to join leg extensions may interlock as pivoting structures, providing relative rotation of the terminal junctions of proximal leg extensions with respect to one another.

A proximal portion of the leg extensions and proximal junctions 228, 230 are configured to contact the vessel wall proximally of the location of anchoring legs 210, 212 and on different circumferential surfaces of the vessel. Using a combination of anchoring legs having different contact surfaces along the axial length of the neighboring (e.g., parent) vessel and different contact surfaces along the circumference of the vessel generally provides stable anchoring of the device without damaging the vessel wall and without interfering with flow in the neighboring vessel. Both sets of anchoring legs are generally atraumatic to tissue and contact the vessel walls over an extended surface area.

Figure 12C:
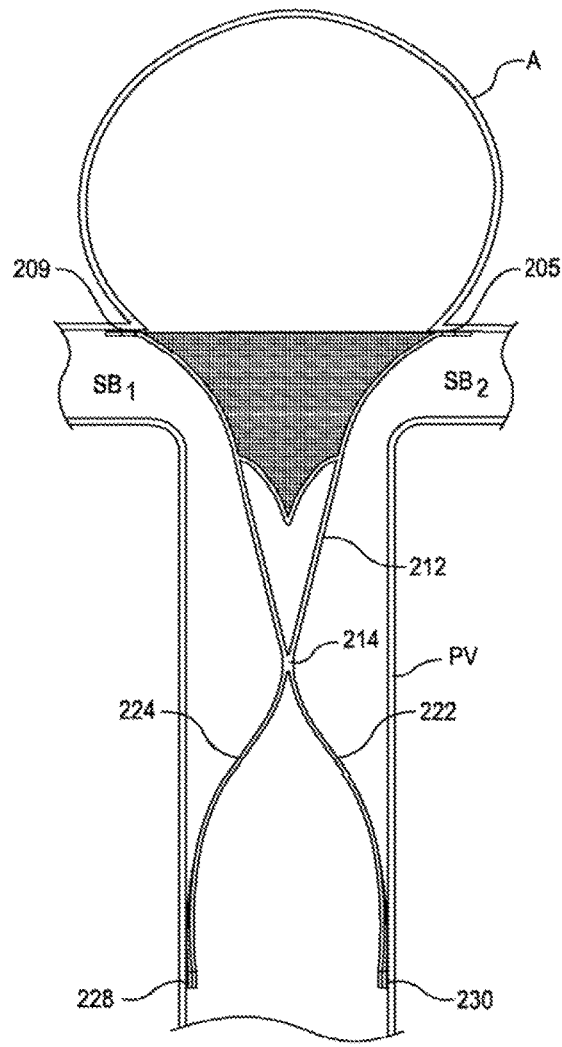
Figure 12D:
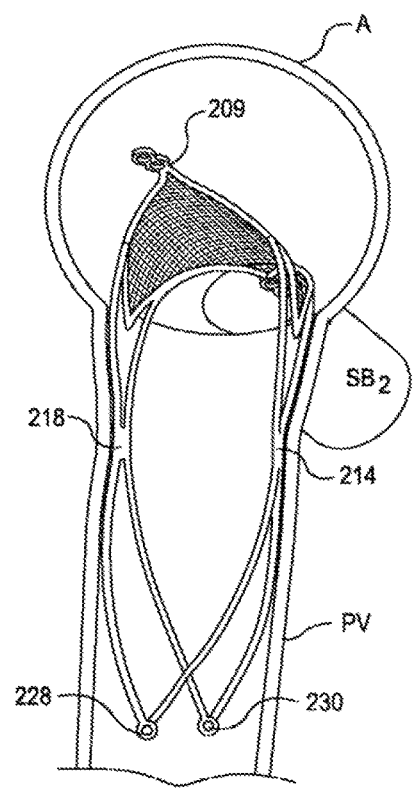

FIGS. 12C and 12D illustrate implantable device 200 in a deployed condition placed across the neck of aneurysm A. When deployed and positioned across the neck of an aneurysm (or another opening), the inverted, substantially U-shaped perimeter support structure and associated closure membrane substantially cover the neck of the aneurysm and extend circumferentially to contact tissue surround both sides of the neck of the aneurysm, or the vessel wall adjacent the neck of the aneurysm, at locations between the lateral corners 205, 209 and proximal to the longitudinal centerline CL of the device. In the embodiments schematically illustrated in FIGS. 12C and 12D, for example, areas of the perimeter support structure and closure membrane proximal to the longitudinal centerline CL and distal to anchoring legs 210, 212 generally contact and support tissue, including the vessel wall, located circumferentially of and in proximity to the neck of the aneurysm. Anchoring legs 210, 212 contact the wall of a neighboring vessel, such as parent vessel PV, along substantially opposite contact surface areas. Proximal anchoring leg segments extending between junctions 214, 218 and 230, 228 and proximal junctions 230, 228 contact the wall of the neighboring vessel, such as parent vessel PV, in locations proximal to those contacted by anchoring legs 210, 212 and along different circumferential surface areas. This embodiment provides enhanced anchoring and support of the implantable device without damaging the vessel wall structure or tissue and without impeding flow in the parent vessel or neighboring vessels.

Figure 13A:
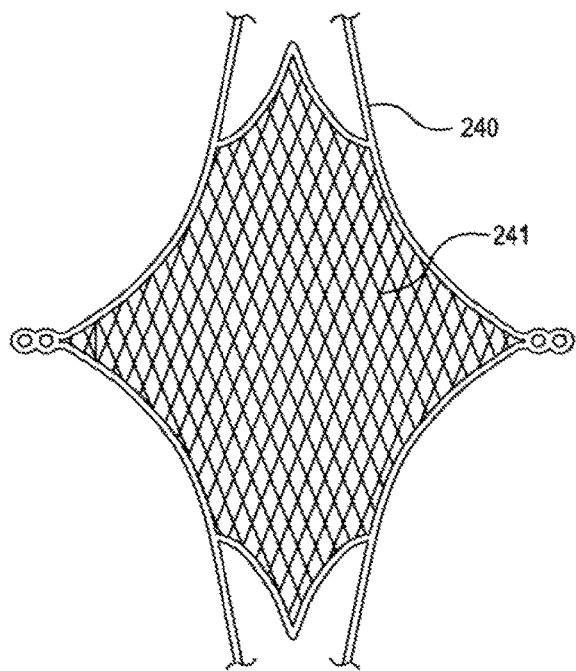
FIGS. 13A-13G show schematic plan views of various embodiments of framework structures and cover membranes.
Figure 13B:
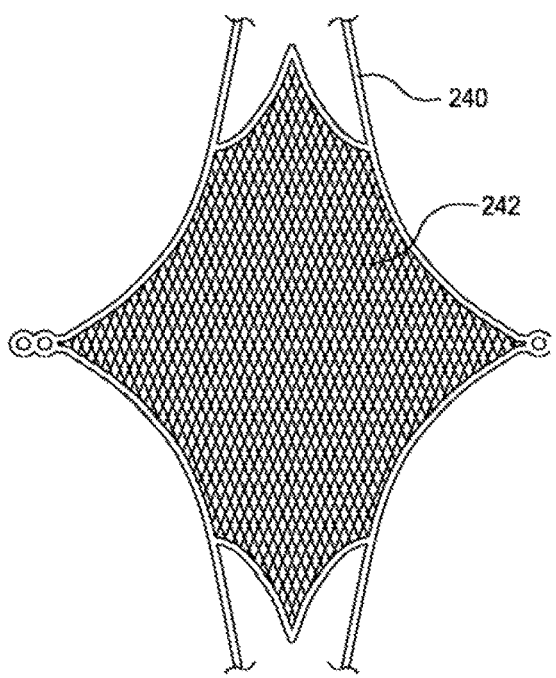
Figure 13C:
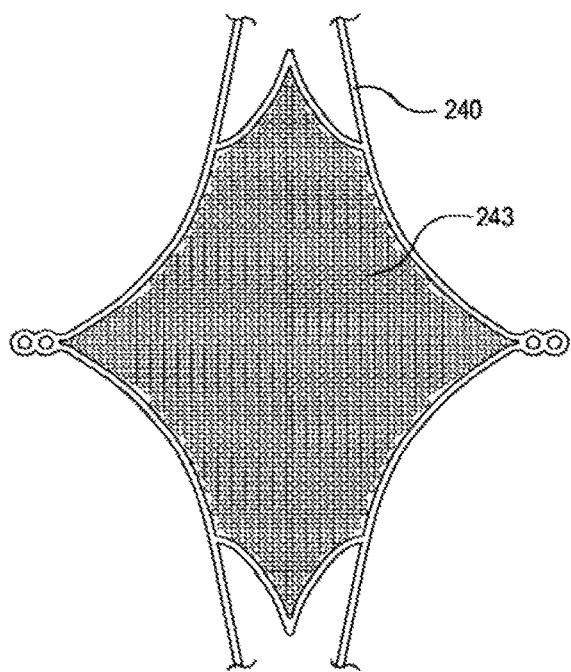
Figure 13D:
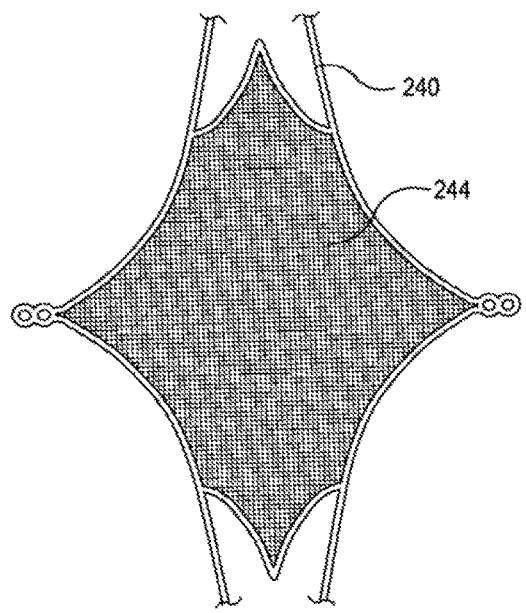
Figure 13E:
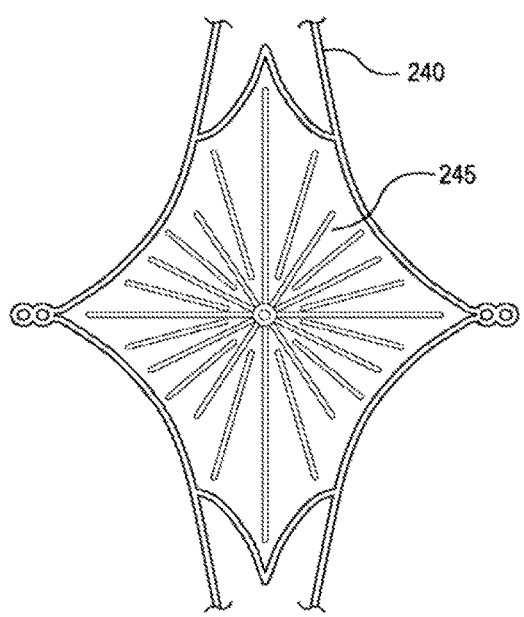
Figure 13F:
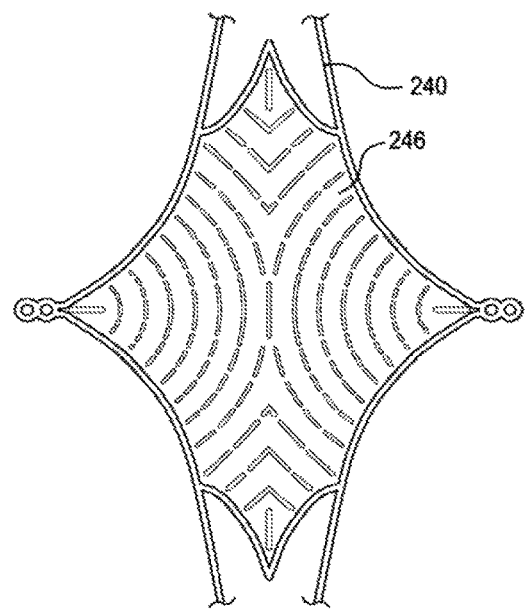
Figure 13G:
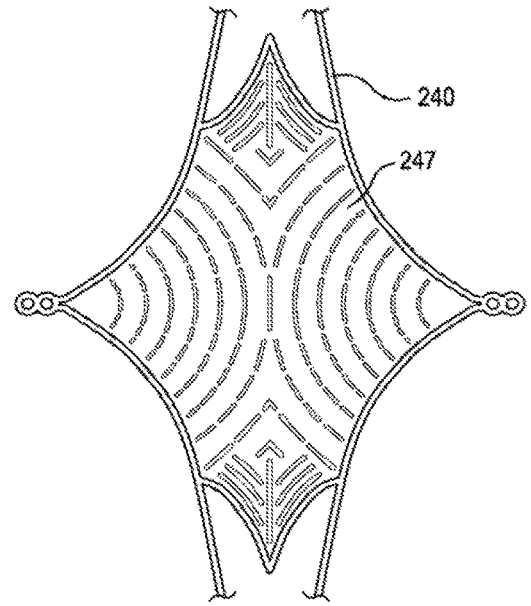

FIGS. 13A-13G illustrate a variety of different types of membranes and cover structures. In each of these diagrams, a framework support structure having a modified diamond-shaped configuration formed by framework sides having a complex, curved configuration of the type illustrated in FIGS. 12A and 12B is shown, with a mesh-like structure or membrane provided substantially coextensive with the internal space formed by the framework structure. FIG. 13A shows a framework structure 240 in combination with a mesh-like cover structure 241 having relatively large openings in the mesh-like structure arranged in a repeating diamond configuration. FIG. 13B shows a framework structure 240 in combination with a mesh-like cover structure 242 having relatively small openings in a mesh-like structure arranged in a repeating diamond configuration. FIG. 13C shows a framework structure 240 in combination with a mesh-like cover structure 243 having relatively small circular openings, or pores arranged substantially uniformly over its surface area. FIG. 13D shows a framework structure 240 in combination with a mesh-like cover structure 244 having relatively small openings in the mesh-like structure arranged in a screen-like configuration. FIG. 13E shows a framework structure 240 in combination with a cover structure 245 having an array of generally linear openings with a central opening and terminus. This embodiment may facilitate folding and deployment of the membrane. FIG. 13F shows a framework structure 240 in combination with a cover structure 246 having two arrays of perforations arranged in curves facing the lateral corners and two arrays of generally linear perforations arranged in a chevron-like configuration lacing the axial corners of the framework structure. This embodiment may facilitate folding and deployment of the membrane. FIG. 13G shows a framework structure 240 in combination with a cover structure 247 having two arrays of perforations arranged in curves facing the lateral corners and two arrays of perforations generally facing the axial corners of the framework structure. This embodiment may also facilitate folding and deployment of the membrane. It will be appreciated that many different configurations of mesh-like, perforated and porous membrane structures may be provided.

Figure 14A:
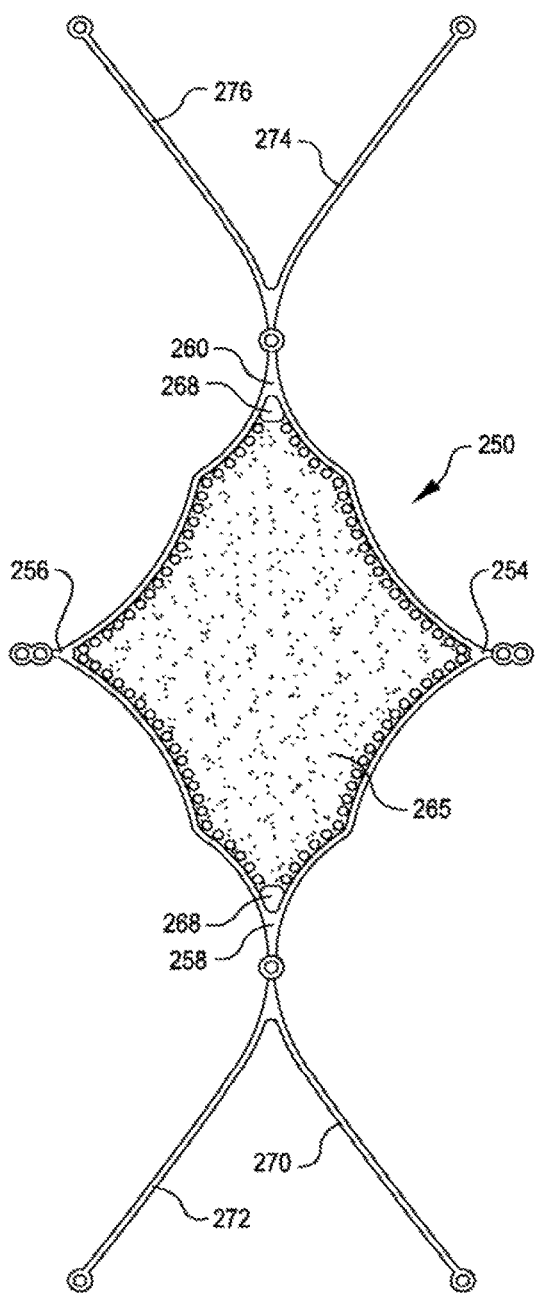
FIG. 14A shows a plan view of a device of the present invention in a substantially flat, pre-assembled form having a perforated cover structure
Figure 14B:
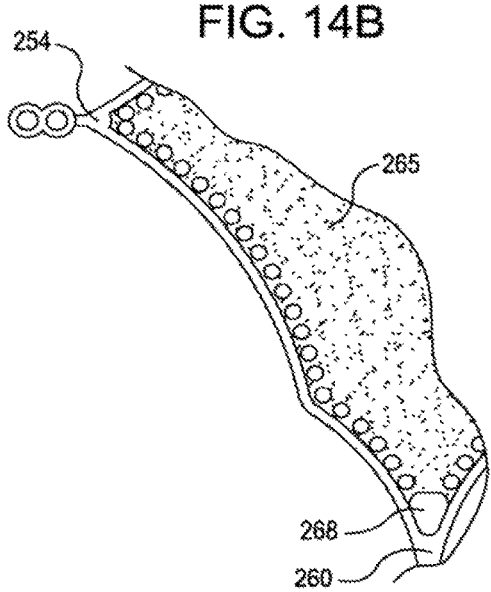
FIG. 14B shows an enlarged view of a portion of the perforated cover structure shown in FIG. 14A.

FIGS. 14A and 14B illustrate yet another embodiment of an implantable device of the present invention having a membrane substantially covering the internal space of both the framework support structure and the anchoring legs. Implantable device 250, as shown, comprises a framework perimeter support structure 252 composed of lour substantially similar segments joined at longitudinal corners 254, 256 and axial corners 258, 260. Closure membrane 265 substantially fills the internal space of the framework support structure and has pores 266 along contact edges with the framework perimeter support structure 252. Enlarged pores 268 may be provided in proximity to corners, such as at axial corners 258, 260. Implantable device 250 additionally has proximal anchoring leg segments 270, 272, 274, 276 that may be joined as described above with reference to FIGS. 12A and 12B to provide proximal anchoring leg segments lying in a different plane from the more distal located anchoring legs.

FIGS. 16A and 16B illustrate a generally inverted U-shaped framework support structure 280, 290 without a membrane, incorporating an additional frame element 281, 291 extending between lateral corners 282, 284 and 292, 294 of framework support structure 280, 290, respectively. Implantable device 280 has an anchoring leg structure similar to that illustrated and described with reference to FIG. 7A; implantable device 290 has an anchoring leg structure, with proximal leg extensions, similar to that illustrated and described with reference to FIG. 12B. It will be appreciated that additional frame elements having many different configurations may be provided to enhance the structural stability of the framework support structure, to provide additional attachment points for membranes or radiopaque markers, or for other reasons.

While in the foregoing specification this invention has been described in relation to certain preferred embodiments thereof, and many details have been set forth for purposes of illustration, it will be apparent to those skilled in the art that the invention is susceptible to various changes and modifications as well as additional embodiments, and that certain of the details described herein may be varied considerably without departing from the basic spirit and scope of the invention.

We claim:

1. An implantable device for treating a blood vessel having a physiological cavity, the implantable device comprising:
   a body frame having a flow diverting section at a distal end and an anchoring section at a proximal end, a longitudinal axis extending from the distal end to the proximal end of the body frame, a first orthogonal axis substantially perpendicular to the longitudinal axis, and a second orthogonal axis substantially perpendicular to the longitudinal axis and the first orthogonal axis;
   the flow diverting section of the body frame comprising a first pair of free ends, each of the first pair of free ends being longitudinally aligned along the first orthogonal axis and forming the distal end of the body frame allowing for positioning adjacent to or within the physiological cavity,
   a first pair of anchoring segments and a second pair of anchoring segments being longitudinally aligned along the second orthogonal axis;
   where the flow diverting section is folded about the first orthogonal axis such that the first pair of anchoring segments and the second pair of anchoring segments extend proximally from the flow diverting section on either side of the first pair of free ends to form the anchoring section and when deployed the first pair of anchoring segments expands away from the second pair of anchoring segments along the second orthogonal axis to anchor within a stem blood vessel at a blood vessel bifurcation, the stem blood vessel extending opposite the physiological cavity; and
   a semi-occlusive flow diverting surface extending within a portion of the body frame between the first pair of free ends such the flow diverting surface partially occludes the physiological cavity while allowing flow along the first orthogonal axis adjacent to the flow diverting surface.

2. The implantable device of claim 1, where the body frame self-expands from a delivery condition to a deployed condition, a profile of the deployed condition being larger than a profile of the delivery condition.

3. The implantable device of claim 1, where the semi-occlusive flow diverting surface forms a curved surface when the flow diverting section is folded about the first orthogonal axis.

4. The implantable device of claim 1, further comprising at least one anchoring element extending proximally from at least one of the first pair of anchoring segments and the second pair of anchoring segments.

5. An implantable device for diverting blood flow from a physiological cavity, the implantable device comprising:
   a body frame having a blocking section at a distal end and an anchoring section at a proximal end, a longitudinal axis extending from the distal end to the proximal end of the body frame, a first orthogonal axis substantially perpendicular to the longitudinal axis, and a second orthogonal axis substantially perpendicular to the longitudinal axis and the first orthogonal axis;
   the blocking section of the body frame comprising a first pair of free ends, each end of the first pair of free ends being longitudinally aligned along the first orthogonal axis and forming the distal end of the body frame allowing for positioning adjacent to or within the physiological cavity such that the first orthogonal axis runs parallel to a side branch vessel at a vessel bifurcation;
   a first pair of anchoring segments and a second pair of anchoring segments being longitudinally aligned along the second orthogonal axis;
   where the blocking section is folded about the first orthogonal axis such that the first pair of anchoring segments and the second pair of anchoring segments extends proximally from the blocking section on either side of the first pair of free ends to form the anchoring section and when deployed the first pair of anchoring segments expands away from the second pair of anchoring segments along the second orthogonal axis to anchor within a stem vessel, the stem vessel feeding the side branch vessel at the bifurcation; and
   a semi-occlusive blocking surface extending within a portion of the body frame between the first pair of free ends such that the blocking surface partially occludes the physiological cavity while allowing flow along the first orthogonal axis within the side branch vessel.

6. The implantable device of claim 5, where the body frame self-expands from a delivery condition to a deployed condition, a profile of the deployed condition being larger than a profile of the delivery condition.

7. The implantable device of claim 5, where the semi-occlusive blocking surface forms a curved surface when the blocking section is folded about the first axis.

8. The implantable device of claim 5, further comprising at least one anchoring element extending proximally from at least one of the first pair of anchoring segments and the second pair of anchoring segments.

* * * * *